(12) United States Patent
Long et al.

(10) Patent No.: US 8,444,646 B2
(45) Date of Patent: May 21, 2013

(54) BONE PREPARATION TOOL KIT AND ASSOCIATED METHOD

(75) Inventors: Jack F. Long, Warsaw, IN (US); Michael E. Coon, Warsaw, IN (US)

(73) Assignee: DePuy Products, Inc., Warsaw, IN (US)

( * ) Notice: Subject to any disclaimer, the term of this patent is extended or adjusted under 35 U.S.C. 154(b) by 792 days.

(21) Appl. No.: 12/421,335

(22) Filed: Apr. 9, 2009

(65) Prior Publication Data

US 2009/0198238 A1  Aug. 6, 2009

Related U.S. Application Data

(62) Division of application No. 10/403,708, filed on Mar. 31, 2003, now Pat. No. 7,517,364.

(51) Int. Cl.
*A61B 17/17* (2006.01)
*A61B 17/90* (2006.01)

(52) U.S. Cl.
USPC .................. 606/79; 606/86 R; 623/19.14

(58) Field of Classification Search
USPC ............ 606/79–80, 86 R, 87, 167–168, 170, 606/180; 623/17.14, 18.11, 19.11–19.14
See application file for complete search history.

(56) References Cited

U.S. PATENT DOCUMENTS

| | | | |
|---|---|---|---|
| 788,362 A | 4/1905 | Lavery | |
| 1,023,542 A | 4/1912 | Winter | |
| 1,345,443 A | 7/1920 | Hood | |
| 1,669,701 A | 5/1928 | Estwing | |
| 2,200,120 A | 5/1940 | Nauth | |
| 2,222,517 A | 11/1940 | Price | |
| 2,243,718 A | 5/1941 | Moreira | |
| 2,718,228 A | 9/1955 | Van Steenbrugghe | |
| 2,725,878 A | 12/1955 | Reiter | |
| 2,804,895 A | 9/1957 | Clement | |
| 2,934,065 A | 4/1960 | Townley | |
| 3,002,514 A | 10/1961 | Deyerle | |

(Continued)

FOREIGN PATENT DOCUMENTS

| | | |
|---|---|---|
| DE | 2041929 | 8/1970 |
| DE | 4228710 | 8/1992 |

(Continued)

OTHER PUBLICATIONS

Biomet brochure (engineering drawings).

(Continued)

*Primary Examiner* — Kevin T Truong
*Assistant Examiner* — Larry E Waggle, Jr.
(74) *Attorney, Agent, or Firm* — Maginot, Moore & Beck LLP

(57) ABSTRACT

A prosthesis (20) for use in performing joint arthroplasty is provided. The prosthesis (20) is to be fitted to a long bone (3). The prosthesis includes a first body (22) having a first body articulating surface (24) defining a generally circular outer periphery (26) of the first body articulating surface (24). The first body (22) has a support surface (28) opposed to the articulating surface (24). The support surface (28) is adapted to receive the head of the long bone (3). The prosthesis (20) also includes a second body (30) operably associated with the first body (22). The second body (30) has a second body articulating surface (32) extending from a portion of the circular outer periphery (26) of the first body articulating surface (24). A tool kit for preparing a humerus to receive a prosthesis is also disclosed.

20 Claims, 24 Drawing Sheets

U.S. PATENT DOCUMENTS

| | | |
|---|---|---|
| 3,605,527 A | 9/1971 | Gambale |
| 3,702,611 A | 11/1972 | Fishbein |
| 3,840,904 A | 10/1974 | Tronzo |
| 3,855,638 A | 12/1974 | Pilliar |
| 3,979,778 A | 9/1976 | Stroot |
| 4,042,980 A | 8/1977 | Swanson et al. |
| 4,206,517 A | 6/1980 | Pappas et al. |
| 4,271,849 A | 6/1981 | Rehder |
| 4,274,164 A | 6/1981 | Rehder et al. |
| 4,328,593 A | 5/1982 | Sutter et al. |
| 4,332,036 A | 6/1982 | Sutter et al. |
| 4,335,429 A | 6/1982 | Kawakatsu |
| 4,355,429 A | 10/1982 | Mittelmeier et al. |
| 4,432,358 A | 2/1984 | Fixel |
| 4,441,492 A | 4/1984 | Rydell et al. |
| 4,502,474 A | 3/1985 | Comparetto |
| 4,550,450 A | 11/1985 | Kinnett |
| 4,601,289 A | 7/1986 | Chiarizzio et al. |
| 4,714,471 A | 12/1987 | Grundei |
| 4,722,330 A | 2/1988 | Russell et al. |
| 4,752,296 A | 6/1988 | Buechel et al. |
| 4,787,378 A | 11/1988 | Sodhi |
| 4,795,473 A | 1/1989 | Grimes |
| 4,801,289 A | 1/1989 | Sugimoto et al. |
| 4,805,607 A | 2/1989 | Engelhardt et al. |
| 4,846,841 A | 7/1989 | Oh |
| 4,865,605 A | 9/1989 | Dines et al. |
| 4,865,609 A | 9/1989 | Roche |
| 4,893,619 A | 1/1990 | Dale et al. |
| 4,919,669 A | 4/1990 | Lannelongue |
| 4,987,904 A | 1/1991 | Wilson |
| 4,995,883 A | 2/1991 | Demane et al. |
| 5,041,117 A | 8/1991 | Engelhardt |
| 5,064,427 A | 11/1991 | Burkinshaw |
| 5,070,623 A | 12/1991 | Barnes |
| 5,108,396 A | 4/1992 | Lackey et al. |
| 5,116,339 A | 5/1992 | Glock |
| 5,141,520 A | 8/1992 | Goble et al. |
| 5,226,915 A | 7/1993 | Bertin |
| 5,250,051 A | 10/1993 | Maryan |
| 5,258,033 A | 11/1993 | Lawes et al. |
| 5,282,865 A | 2/1994 | Dong |
| 5,312,411 A * | 5/1994 | Steele et al. ............ 606/88 |
| 5,314,479 A | 5/1994 | Rockwood, Jr. et al. |
| 5,358,525 A | 10/1994 | Fox et al. |
| 5,374,269 A | 12/1994 | Rosenberg |
| 5,405,349 A * | 4/1995 | Burkinshaw et al. ......... 606/88 |
| 5,423,827 A | 6/1995 | Mumme et al. |
| 5,454,816 A | 10/1995 | Ashby |
| 5,470,336 A | 11/1995 | Ling et al. |
| 5,476,467 A | 12/1995 | Benoist |
| 5,486,178 A | 1/1996 | Hodge |
| 5,490,852 A | 2/1996 | Azer et al. |
| 5,507,817 A | 4/1996 | Craig et al. |
| 5,514,139 A | 5/1996 | Goldstein et al. |
| 5,540,696 A | 7/1996 | Booth, Jr. et al. |
| 5,549,704 A | 8/1996 | Sutter |
| 5,569,263 A | 10/1996 | Hein |
| 5,662,476 A | 9/1997 | Ingber et al. |
| 5,683,395 A | 11/1997 | Mikhail |
| 5,690,636 A | 11/1997 | Wildgoose et al. |
| 5,702,460 A | 12/1997 | Carls et al. |
| 5,723,018 A | 3/1998 | Cyprien et al. |
| 5,735,905 A | 4/1998 | Parr |
| 5,769,852 A | 6/1998 | Branemark |
| 5,776,194 A | 7/1998 | Mikol et al. |
| 5,776,201 A | 7/1998 | Colleran et al. |
| 5,779,710 A | 7/1998 | Matsen, III |
| 5,800,437 A | 9/1998 | Gustilo et al. |
| 5,800,557 A | 9/1998 | Elhami |
| 5,830,216 A | 11/1998 | Insall et al. |
| 5,893,850 A | 4/1999 | Cachia |
| 5,957,926 A | 9/1999 | Masini |
| 6,013,104 A | 1/2000 | Kampner |
| 6,045,582 A | 4/2000 | Prybyla |
| 6,063,124 A | 5/2000 | Amstutz |
| 6,071,311 A | 6/2000 | O'Neil et al. |
| 6,093,124 A | 7/2000 | Eyley |
| 6,102,916 A | 8/2000 | Masini |
| 6,110,200 A | 8/2000 | Hinnenkamp |
| 6,127,596 A | 10/2000 | Brown et al. |
| 6,129,764 A | 10/2000 | Servidio |
| 6,132,469 A | 10/2000 | Schroeder |
| 6,156,069 A | 12/2000 | Amstutz |
| 6,168,628 B1 | 1/2001 | Huebner |
| 6,187,012 B1 | 2/2001 | Masini |
| 6,190,390 B1 | 2/2001 | McAllister |
| 6,200,319 B1 | 3/2001 | Storer et al. |
| 6,206,884 B1 | 3/2001 | Masini |
| 6,283,999 B1 | 9/2001 | Rockwood, Jr. |
| 6,319,104 B1 | 11/2001 | Emter |
| 6,334,874 B1 | 1/2002 | Tornier et al. |
| 6,364,910 B1 | 4/2002 | Shultz et al. |
| 6,368,353 B1 | 4/2002 | Arcand |
| 6,508,840 B1 | 1/2003 | Rockwood, Jr. et al. |
| 6,508,841 B2 | 1/2003 | Martin et al. |
| 6,554,865 B2 | 4/2003 | Grusin et al. |
| 6,709,439 B2 | 3/2004 | Rogers et al. |
| 6,740,120 B1 | 5/2004 | Grimes |
| 6,755,865 B2 | 6/2004 | Tarabishy |
| 6,783,549 B1 * | 8/2004 | Stone et al. ............... 623/19.14 |
| 6,875,222 B2 | 4/2005 | Long et al. |
| 6,942,699 B2 | 9/2005 | Stone et al. |
| 6,979,299 B2 | 12/2005 | Peabody et al. |
| 7,097,397 B2 | 8/2006 | Keightley |
| 7,112,204 B2 | 9/2006 | Justin et al. |
| 7,517,364 B2 | 4/2009 | Long et al. |
| 7,527,631 B2 | 5/2009 | Maroney et al. |
| 8,211,113 B2 | 7/2012 | Brown et al. |
| 2001/0009971 A1 | 7/2001 | Sherts et al. |
| 2001/0037152 A1 | 11/2001 | Rockwood, Jr. |
| 2001/0047210 A1 | 11/2001 | Wolf |
| 2002/0016634 A1 | 2/2002 | Maroney et al. |
| 2002/0099381 A1 * | 7/2002 | Maroney ................ 606/86 |
| 2002/0099445 A1 | 7/2002 | Maroney et al. |
| 2002/0133153 A1 * | 9/2002 | Hyde, Jr. ................ 606/53 |
| 2002/0183849 A1 | 12/2002 | Grusin et al. |
| 2003/0018341 A1 | 1/2003 | Deloge et al. |
| 2003/0114859 A1 | 6/2003 | Grusin et al. |
| 2003/0163202 A1 | 8/2003 | Lakin |
| 2003/0212403 A1 | 11/2003 | Swanson |
| 2004/0122521 A1 | 6/2004 | Lee et al. |
| 2004/0193277 A1 | 9/2004 | Long et al. |
| 2004/0193278 A1 | 9/2004 | Maroney et al. |
| 2005/0065612 A1 | 3/2005 | Winslow |
| 2006/0052791 A1 | 3/2006 | Hagen et al. |
| 2006/0142870 A1 | 6/2006 | Robinson et al. |
| 2008/0004701 A1 | 1/2008 | Axelson et al. |

FOREIGN PATENT DOCUMENTS

| | | |
|---|---|---|
| DE | 4220217 | 12/1993 |
| DE | 10233204 | 7/2002 |
| EP | 0845250 | 11/1997 |
| EP | 0888752 | 7/1998 |
| EP | 0903128 | 9/1998 |
| EP | 1064890 | 6/2000 |
| EP | 1228739 | 8/2002 |
| EP | 1470802 | 10/2004 |
| EP | 1518519 | 3/2005 |
| FR | 2418644 | 3/1978 |
| FR | 2418664 | 3/1978 |
| FR | 2578739 | 9/1986 |
| FR | 2737107 | 7/1995 |
| FR | 2898267 A1 | 9/2007 |
| GB | 764600 | 12/1956 |
| GB | 2259253 | 8/1992 |
| WO | 9415551 | 7/1994 |
| WO | 9522302 | 8/1995 |
| WO | 9807393 | 2/1998 |
| WO | 9937254 | 7/1999 |
| WO | 0113823 | 8/2000 |
| WO | 0113823 A3 | 3/2001 |
| WO | 0217822 | 3/2002 |

OTHER PUBLICATIONS

Australian Examiner's Report in corresponding Australian patent application (i.e., AU 2009213073), mailed Feb. 25, 2011 (2 pages).

European Search Report in corresponding European patent application (i.e., EP 10 18 7319), mailed Jan. 13, 2011 (8 pages).
Australian Government—IP Australia, Examiner's First Report on Australian Patent Application No. 2004201199, dated Jan. 9, 2009 (2 pages).
Australian Government—IP Australia, Examiner's First Report on Australian Patent Application No. 2004201349, dated Jun. 4, 2009 (7 pages).
Japan Patent Office, Notification of Reasons for Refusal, corresponding to Japanese Patent Application No. 2004-099913, mailed Feb. 9, 2010 (3 Pages).
DePuy Orthopaedics, Inc. Global Advatage CTA Humeral Head, 2000, 3.5M0460, 0612-03-050 (Rev 3), USA (6 pages).
Biomet Orthopaedics, Inc., Introducing the Copeland Humeral Resurfacing Head, 2001.
Biomet Merck, Ltd., Copeland Surface Replacement Shoulder Arthroplasty, (date unknown).
Endotec, INC. Buechel-Pappas Resurfacing Shoulder System Surgical Procedure by Frederick F. Buechel, M.D. 2001.
Biomet Orthopaedics, Inc., Copeland Humeral Resurfacing Head (date unknown).
European Search Report for European Application No. 04251871.2-1526, Sep. 8, 2004, 3 pages.
European Search Report for European Application No. 05251328.0-2310, Jul. 21, 2005, 4 pages.
European search report dated Dec. 5, 2005, for corresponding EP application 04251913.2.
Biomet brochure (engineering drawings), Jul. 22, 1997.
Depuy Orthopaedics, Inc., Moreland Cemented HIP Revision Instrumentation, (12 Pages Total), 2.3M500, 0602-28-000 (Rev. 6) USA, 1995.
Depuy Orthopaecics, Inc., Moreland Cementless HIP Revision Instrumentation, (12 Pages Total), USA, 1998.
Smith & Nephew, Inc., Orthopaedic Catalog (25 Pages Total) Prepared Oct. 16, 2003, USA.

* cited by examiner

BONE PREPARATION TOOL KIT AND ASSOCIATED METHOD

This application is a divisional of application Ser. No. 10/403,708, filed on Mar. 31, 2003, now U.S. Pat. No. 7,517,364, which issued on Apr. 14, 2009. The disclosure of which is hereby totally incorporated by reference in its entirety.

Cross reference is made to the following applications: U.S. patent application Ser. No. 10/403,707, filed Mar. 31, 2003, now U.S. Pat. No. 7,527,631, which issued on May 5, 2009 entitled "ARTHROPLASTY SIZING GAGE", U.S. patent application Ser. No. 10/403,750, filed Mar. 31, 2003, now abandoned, entitled "ARTICULATING SURFACE REPLACEMENT PROSTHESIS", U.S. patent application Ser. No. 10/403,577, filed Mar. 31, 2003, now abandoned, entitled "MODULAR ARTICULATING SURFACE REPLACEMENT PROSTHESIS", U.S. patent application Ser. No. 10/403,710, filed Mar. 31, 2003, now U.S. Pat. No. 8,366,713, which issued on Feb. 5, 2013, entitled "ARTHROPLASTY INSTRUMENT AND ASSOCIATED METHOD", and U.S. patent application Ser. No. 10/403,364, filed Mar. 31, 2003, now U.S. Pat. No. 7,338,498, which issued on Mar. 4, 2008, entitled "PROSTHETIC IMPLANT, TRIAL AND ASSOCIATED METHOD" filed concurrently herewith which are incorporated herein by reference.

TECHNICAL FIELD OF THE INVENTION

The present invention relates generally to the field of orthopaedics, and more particularly, to an implant for use in arthroplasty.

BACKGROUND OF THE INVENTION

The invention relates to implantable articles and methods for implanting such articles. More particularly, the invention relates to a bone prosthesis and a method for implanting the same.

There are known to exist many designs for and methods of implanting implantable articles, such as bone prostheses. Such bone prostheses include components of artificial joints, such as elbows, hips, knees and shoulders.

Early designs of implantable articles relied upon the use of cements to anchor the implant. However, the current trend is to use cements to a lesser extent because of their tendency to lose adhesive properties over time and the possibility that cement contributes to wear debris within a joint.

Recently, implantable bone prostheses have been designed such that they encourage the growth of hard bone tissue around the implant. Such implants are often implanted without cement and the bone grows around surface irregularities, for example, porous structures on the implant.

One such implantable prosthesis is a shoulder prosthesis. During the lifetime of a patient it may be necessary to perform a total shoulder replacement procedure on a patient as a result of, for example, disease or trauma, for example, disease from osteoarthritis or rheumatoid arthritis. Currently, most implantable shoulder prostheses are total shoulder prostheses. In a total shoulder replacement procedure, a humeral component having a head portion is utilized to replace the natural head portion of the upper arm bone or humerus. The humeral component typically has an elongated intramedullary stem, which is utilized to secure the humeral component to the patient's humerus. In such a total shoulder replacement procedure, the natural glenoid surface of the scapula is resurfaced or otherwise replaced with a glenoid component that provides a bearing surface for the head portion of the humeral component.

With the average age of patients requiring shoulder arthroplasty decreasing, device manufacturers are developing bone sparing implants for the initial treatment of degenerative arthritis. Surface replacement prostheses are being developed to replace the articulating surface of the proximal humerus with a minimal bone resection and minimal disruption of the metaphysis and diaphysis. Current designs utilize a semispherical articular dome with a small stem for rotational stability. The under surface of the articular head is also semispherical and mates with the spherically machined humeral head.

The need for a shoulder replacement procedure may be created by the presence of one of a number of conditions. One such condition is the deterioration of the patient's rotator cuff. Specifically, an intact rotator cuff stabilizes the humeral head in the glenoid fossa of a scapula during abduction of the arm. While it is stabilized in such a manner abduction of the arm causes the humeral head to translate only a short distance in the superior direction (e.g. a few millimeters), whereby a space is maintained between the humeral head and the acromion. However, for patients with rotator cuff arthropathy, significantly greater humeral excursion is observed.

Referring to FIG. 2, a healthy long bone in the form of humerus 1 is shown. The humerus 1 includes a healthy humeral head 2.

Referring now to FIG. 3, a diseased humerus 3 is shown. The diseased humerus 3 includes a diseased or flattened humeral head 4. Whereas the healthy humeral head 2 of the healthy humerus 1 of FIG. 2 has a generally hemispherical shape, the flattened humeral head 4 is quite flat and only slightly domed.

Referring now to FIGS. 4, 5 and 6, a prior art prosthesis 5 is shown. Referring first to FIG. 4, the prosthesis 5 is shown installed on the diseased humerus 3. The prosthesis 5 is positioned over flattened head or bony defect 4. The prosthesis 5 includes a hollow generally hemispherical cup 6. Extending distally from the interior of the cup 6 is a generally conically shaped stem 15 that anchors the prosthesis 5 into the humerus 3.

Referring now to FIGS. 5 and 6, the prosthesis 5 is shown implanted in a shoulder joint. As shown in FIG. 5, the humerus 3 is shown in a position in which the arm is resting against the patient's torso. Articulating surface of the cup 6 of the prosthesis 5 is shown in contact with the scapula 7, the clavicle 8, and the acromion 9. As can be seen in FIG. 5, in this downward position of the humerus 3 the prosthesis 5 provides the articulating surface of cup 6 in contact with the acromion 9, the clavicle 8, and the scapula 7 to provide for a acceptable artificial joint in this position.

However, referring to FIG. 6, the humerus 3 is shown abducted in the direction of arrow 10 such that the long bone or humeral centerline 11 is at an angle $\alpha$ of about fifteen (15) degrees with the vertical centerline 12. As can be seen in FIG. 6, on a slight abduction of fifteen degrees, the acromion 9 is positioned outside the articulating surface 6 of the prosthesis 5 causing the acromion 9 to impinge upon the humerus 3 causing great pain to the patient and severely limited motion of the humerus 3.

In particular, hyper-translation of the humeral head in the superior direction is observed in patients with massive rotator cuff deficiency, thereby resulting in articulation between the superior surface of the humeral head and both the inferior surface of the acromion and the acromioclavicular joint during abduction of the patient's arm. Such articulation between these components accelerates humeral articular destruction and the erosion of the acromion and acromioclavicular joint. Moreover, such bone-to-bone contact is extremely painful for the patient, thereby significantly limiting the patient's range of motion. In short, patients with massive rotator cuff tear and associated glenohumeral arthritis, as is seen in cuff tear arthropathy, may experience severe shoulder pain, as well as reduced function of the shoulder.

In order to treat patients suffering from cuff tear arthropathy, a number of prostheses and techniques utilizing existing prostheses have heretofore been designed. For example, surgeons heretofore utilized a relatively large humeral head prosthesis in an attempt to completely fill the shoulder joint space. It was believed that such use of a large prosthesis would increase the efficiency of the deltoid muscle, thereby improving motion of the shoulder. However, clinical experience has shown that such use of a large humeral head prosthesis (overstuffs) the shoulder joint thereby increasing soft tissue tension, reducing joint range of motion, and increasing shoulder pain. Moreover, such use of an oversized prosthetic head fails to resurface the area of the greater tubercle of the humerus, thereby allowing for bone-to-bone contact between the greater tubercle and the acromion during abduction of the patient's arm.

A number of humeral head bipolar prostheses have also been utilized in an attempt to address the problems associated with cuff tear arthropathy. It was believed that the relatively unstrained motion of the bipolar head would improve shoulder motion. However, heretofore designed bipolar prosthetic heads include relatively large offsets, thereby overstuffing the shoulder joint in a similar manner as described above. Moreover, scar tissue may form around the bipolar head thereby (freezing) the dual articulating motion of the prosthesis that has been known to create a large hemi arthroplasty that likewise overstuffs the shoulder joint. In addition, such bipolar prosthetic heads do not cover the articulating surface between the greater tubercle and the acromion, thereby creating painful bone-to-bone contact between them.

Yet further, a number of techniques have heretofore been designed in which the relatively rough surface of the greater tubercle is resurfaced with an osteotome or high speed burr. Although this approach results in a smoother tubercle contact surface, relatively painful bone-to-bone articulating contact still occurs, thereby reducing the patient's range of motion.

More recently, the assignee of the applicant of the present invention has invented a method and apparatus for performing a shoulder replacement procedure in a treatment of a cuff tear arthroplasty which has been filed in the U.S. Patent and Trademark Office under U.S. application Ser. No. 09/767,473 filed Jan. 23, 2001, hereby incorporated in its entireties by reference in this application. This application provides for a method and apparatus for treating cuff tear arthroplasty utilizing a total shoulder replacement prosthesis. This prosthesis includes an artificial head as well as a stem that extends into a rimmed medullary canal. Such a prosthesis is limited to use with a total shoulder prosthesis and is not suitable for use with bone sparing implants for the initial treatment of the degenerative arthritis.

What is needed, therefore, is a method and apparatus for performing bone sparing arthroplasty shoulder replacement surgery utilizing bone sparing implants for the initial treatment of degenerative arthritis, which will be useful in the treatment of cuff tear arthroplasty, which overcomes one or more of the aforementioned drawbacks. What is particularly-needed is a method and apparatus for performing a bone sparing implant shoulder procedure that eliminates painful articulation between the great tubercle of the humerus and the acromion.

SUMMARY OF THE INVENTION

The present invention provides for an extended articulation resurfacing shoulder that provides a low-friction prosthetic bearing surface for articulation between the greater tuberosity and the acromion. Such a prosthesis is utilized with a bone sparing minimal resection of a portion of the humeral head.

The present invention provides for an extended articulation resurfacing shoulder with superior/lateral flange for extended articulation into the coracoacromial arch.

According to one embodiment of the present invention, a prosthesis for use in performing joint arthroplasty is provided. The prosthesis is to be fitted to a long bone. The prosthesis includes a first body having a first body articulating surface defining a generally circular outer periphery of the first body articulating surface. The first body has a support surface opposed to first body articulating surface. The support surface is adapted to receive the head of the long bone. The prosthesis also includes a second body operably associated with the first body. The second body has a second body articulating surface extending from a portion of the circular outer periphery of the first body articulating surface.

According to another embodiment of the present invention, a tool kit for preparing a humerus to receive a prosthesis is provided. The prosthesis has a first body having a first articulating surface and an opposed first support surface and has a second body having a second articulating surface and an opposed second support surface. The kit is used to prepare the humerus to receive the prosthesis. The tool kit includes a reamer for preparing a first prepared surface on the humerus. The first prepared surface receives the first support surface. The tool kit also includes a bone cutting tool for preparing a second prepared surface on the humerus. The second prepared surface receives the second support surface.

According to a further embodiment of the present invention, a method for performing shoulder arthroplasty for an indication of rotator cuff tear arthropathy is provided. The method includes the step of providing a prosthesis with a first body having a first articulating surface and an opposed first support surface and with a second body having a second articulating surface and an opposed second support surface. The method also includes the step of providing a tool kit for preparing a humerus for receiving the prosthesis. The method includes the step of preparing a first prepared surface for cooperation with the first support surface with the tool kit. The method further includes the step of preparing a second prepared surface for cooperation with the second support surface with the tool kit. The method also includes the step of implanting the prosthesis onto the first prepared surface and the second prepared surface. The method also includes the step of providing an instrument for preparing a surface on a long bone, providing a plurality of trials, each of said trials being adapted to mate with the surface, selecting one of the plurality of trials, performing a trial reduction on said one of said plurality of trials, determining if said one of said plurality of trials is satisfactory, performing additional trial reductions as required, selecting one of a plurality of joint prostheses corresponding to one of said plurality of trials based upon the trial reductions, and implanting the selected one prosthesis onto the long bone.

The technical advantage of the present invention includes the ability to provide a low friction bearing surface between the greater tuberosity and the acromion. For example, according to one aspect of the present invention, a superior/lateral flange extends from a periphery of the hemispherical body of the prosthesis, which flange provides for extended articulation in the coracoacromial arch. Thus, the present invention provides a low friction bearing surface between the greater tuberosity and the acromion.

The technical advantages of the present invention further include the ability to provide for an effective remedy for rotator cuff tear arthropathy as part of a bone saving surgical procedure. For example, according to one aspect of the present invention, a prosthesis is provided which includes a generally hollow hemispherical body which mates with a slightly resected humeral head. Thus, the present invention provides for a surgical procedure with minimal bone loss.

Other technical advantages of the present invention will be readily apparent to one skilled in the art from the following figures, descriptions and claims.

BRIEF DESCRIPTION OF THE DRAWINGS

For a more complete understanding of the present invention and the advantages thereof, reference is now made to the following description taken in connection with the accompanying drawings, in which.

DETAILED DESCRIPTION OF THE INVENTION

Embodiments of the present invention and the advantages thereof are best understood by referring to the following descriptions and drawings, wherein like numerals are used for like and corresponding parts of the drawings.

Figure 7:
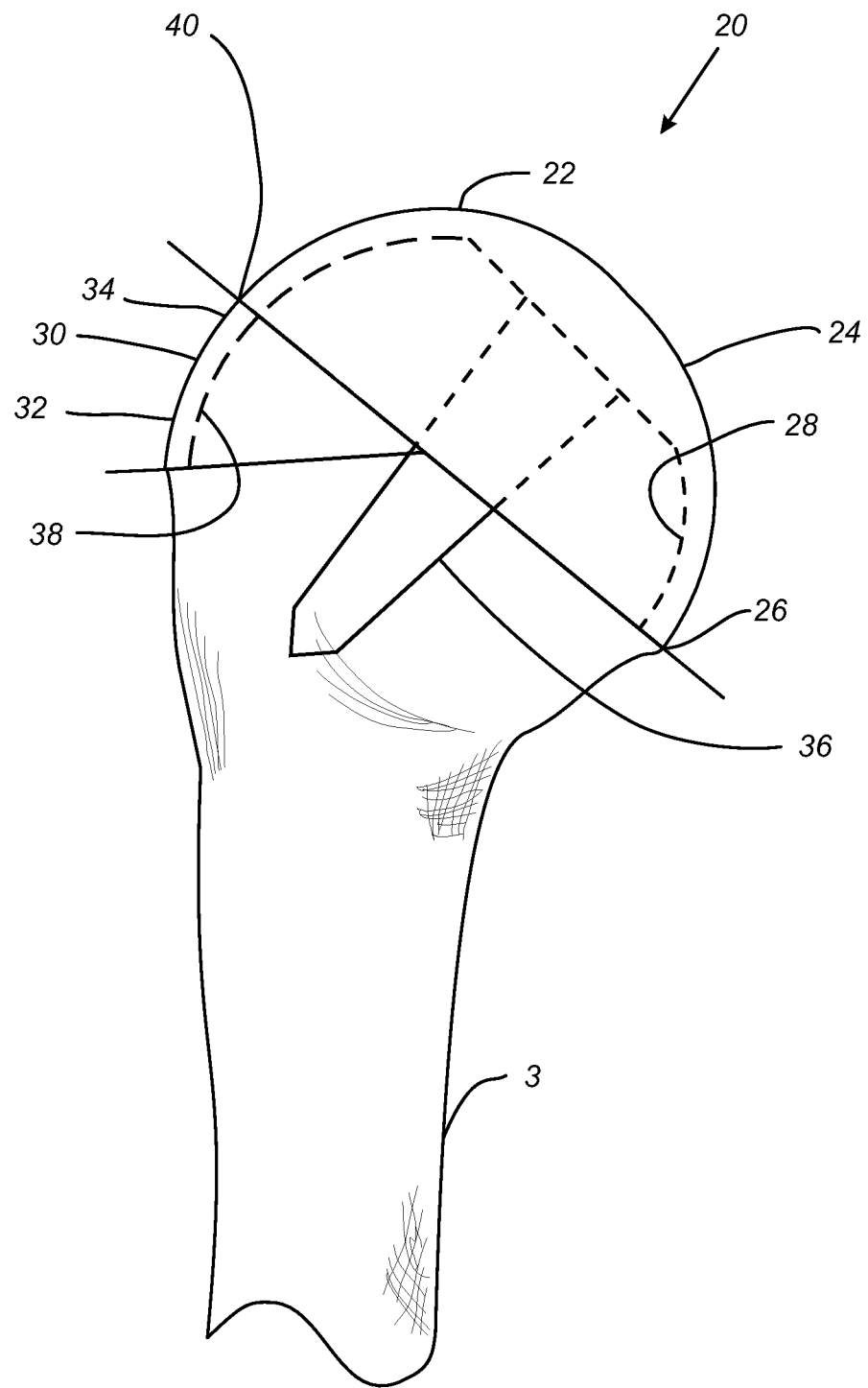
FIG. 7 is an enlarged plan view of the extended head humeral prosthesis of FIG. 1.

Referring now to FIG. 7, an embodiment of the present invention is shown as prosthesis 20. The prosthesis 20 is used in performing bone preserving joint arthroplasty. The prosthesis 20 is to be fitted to the head of a long bone. For example, the long bone as shown in FIG. 7 is in the form of humerus 3. The prosthesis 20 includes a first body 22 having an articulating surface 24 defining a generally circular outer periphery 26. The first body 22 also includes a second surface 28 opposed to the articulating surface 24. The second surface 28 is adapted to receive the head of the humerus 3.

The prosthesis 20 further includes a second body 30 operably associated with the first body 22. The second body 30 has a second body articulating surface 32 extending from a portion 34 of the circular periphery 26 of the first articulating surface 24. The second body articulating surface 32 is adapted to prevent impingement of the acromion 9 (see FIG. 1) with the humerus 3 when the humerus 3 is in the abducted position (see FIG. 8).

While the prosthesis of the present invention may be secured to the humerus by securing of the second surface 28 to the humerus and bony ingrowth there between, preferably and as shown in FIG. 7, the prosthesis 20 further includes a stem 36 operably associated with the first body 22 or the second body 30. As shown in FIG. 7, the stem 36 is associated with the first body 22. The stem 36 is adapted to assist in securing the prosthesis 20 to the humerus 3. As shown in FIG. 7, the prosthesis 20 is an integral or one-piece item. It should be appreciated that the prosthesis 20 may be modular. For example, the stem 36 may be a separate component from the first body 22 or the second body 30. Likewise, the second body 30 may be a separate component from the first body 22.

As shown in FIG. 7, the first body 22 may have any shape capable for articulating motion with the glenoid cavity (see FIG. 8), however, preferably the articulating surface 24 is generally convex. For example, and as shown in FIG. 7, the articulating surface 24 may be generally hemispherical. Likewise, the second surface 28 may likewise be generally hemispherical with the first body 22 being generally a hollow hemisphere. Similarly, the second body articulating surface 32 is preferably convex and may have a generally spherical shape. Likewise, the second body second surface 38 may likewise be generally spherical. The second body 30 may thus also be generally a sector of a hollow sphere.

To provide for smooth motion of the humerus 3 through the abduction of the humerus 3 with respect to glenoid cavity 14 (see FIG. 8) boundary portion 40 of the prosthesis 20 located between the second articulating surface 32 and the first articulating surface 24 where the second articulating surface 32 extends from the first articulating surface 24 is generally smooth and continuous.

Figure 1:
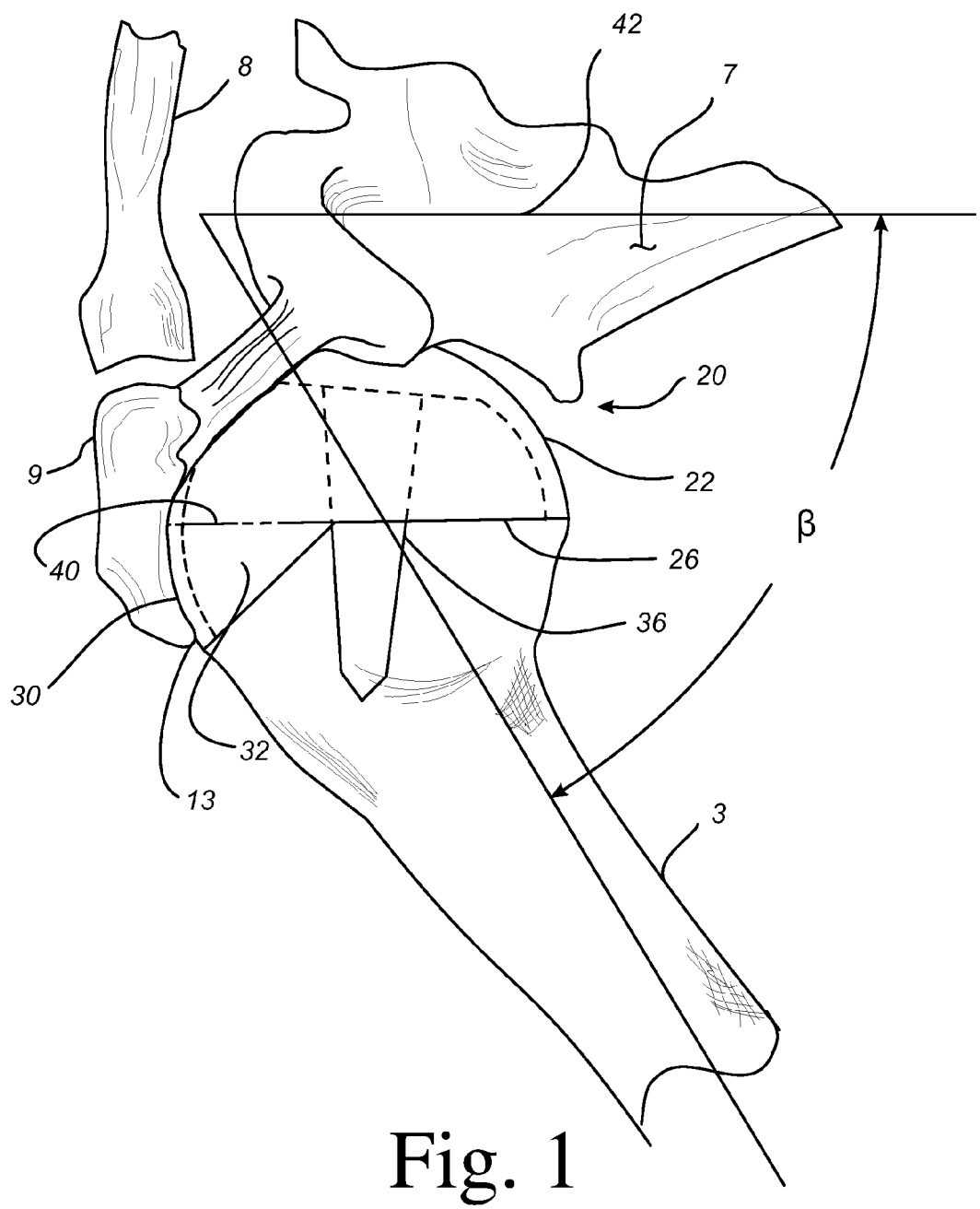
FIG. 1 is a plan view of a extended head humeral prosthesis according to the present invention shown in position implanted on a diseased humerus.
Figure 2:
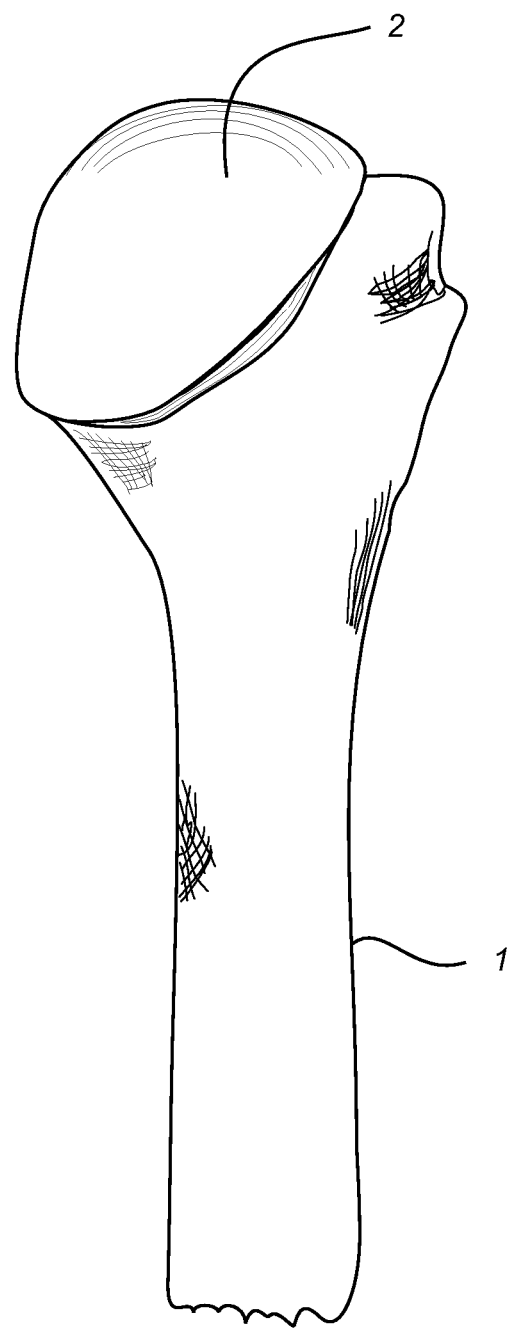
FIG. 2 is a plan view of a healthy humerus.
Figure 3:
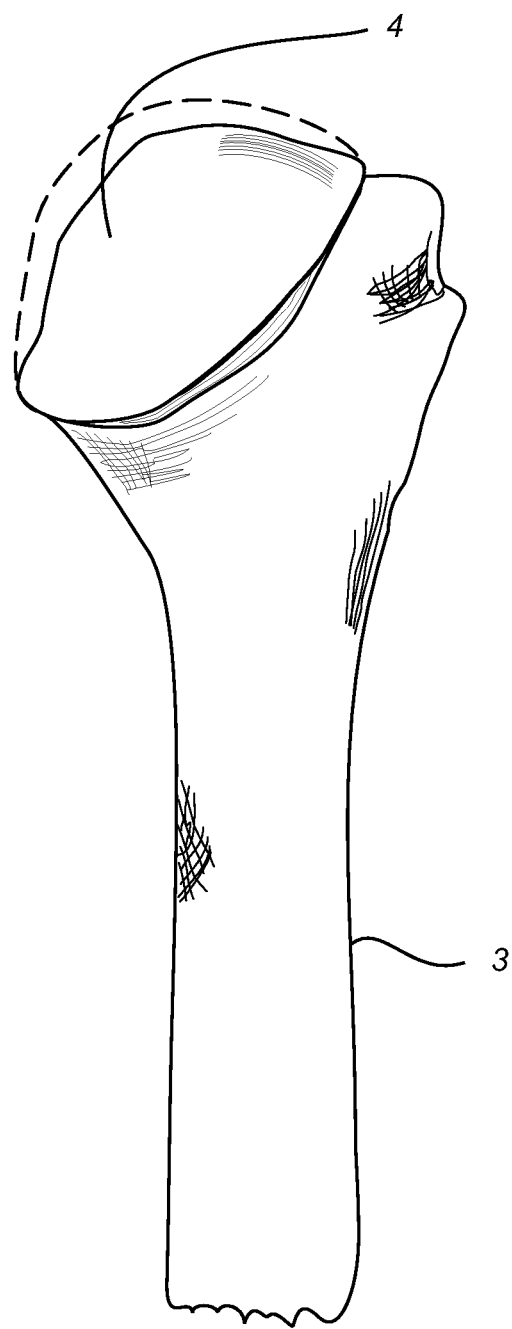
FIG. 3 is a plan view of a diseased humerus.
Figure 4:
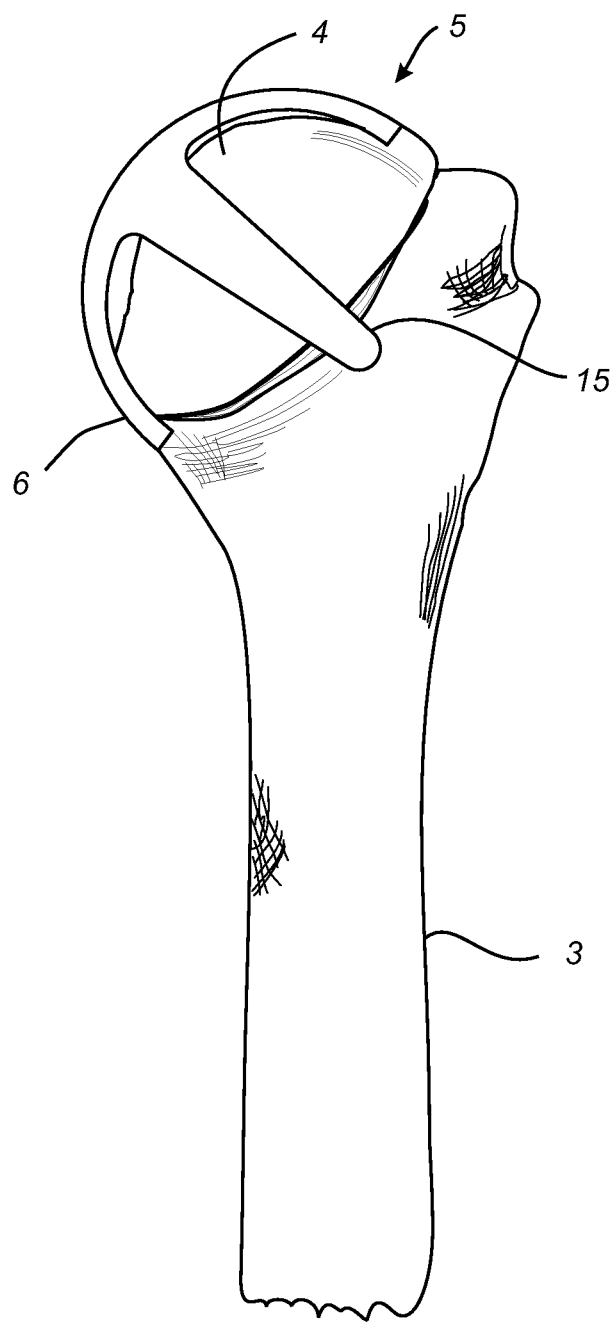
FIG. 4 is a plan view of a prior art humeral prosthesis.
Figure 5:
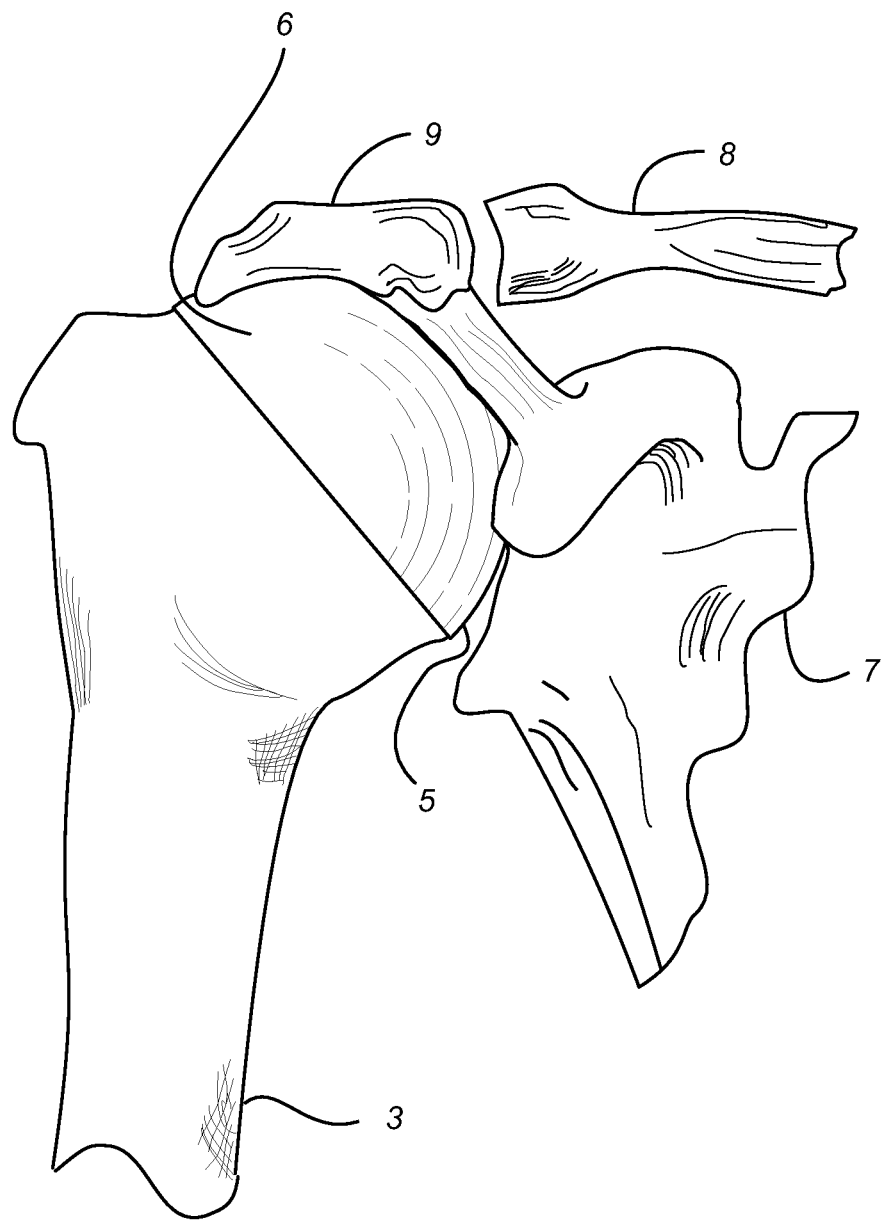
FIG. 5 is a plan view of a prior art humeral prosthesis shown in position implanted on a diseased humerus with the humerus shown in the retracted position.
Figure 6:
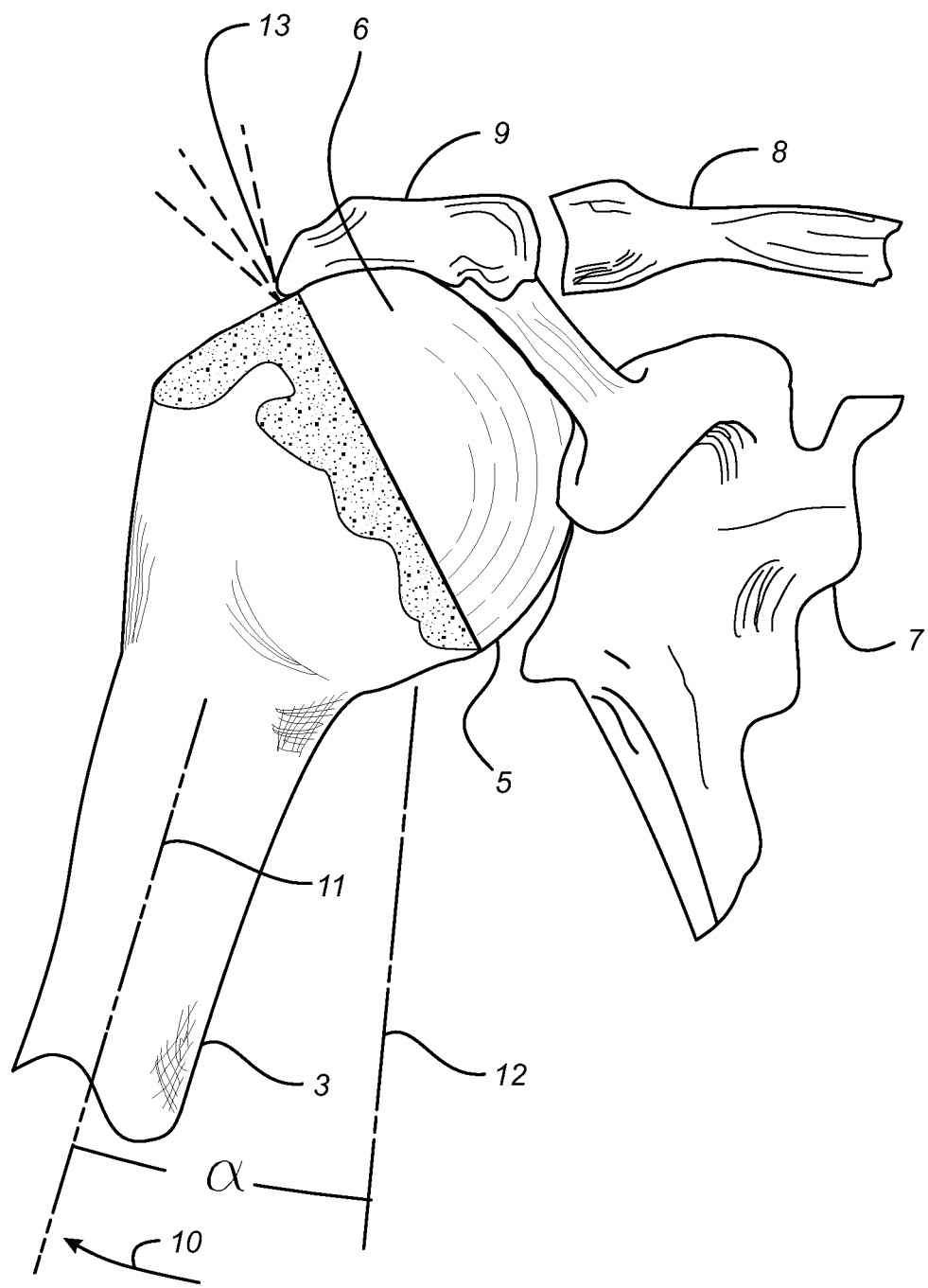
FIG. 6 is a plan view of a prior art humeral prosthesis shown in position implanted on a diseased humerus with the humerus shown in the extended position with the humerus impinged on the distal acromion.

Referring now to FIG. 1, the prosthesis 20 of the present invention is shown installed in the humerus 3 with the adjacent bones of the clavicle 8, scapula 7 and acromion 9 shown in position. As shown in FIG. 1, the humerus 3 is abducted into an angle β with respect to vertical erect body reference line 42. As can be seen in FIG. 3, the acromion 9 extends past the boundary portion 40 separating the first body 22 of the prosthesis 20 from the second body 30 of the prosthesis 20. Thus, the second body articulating surface 32 is utilized to prevent the acromion 9 from impinging on the humerus 3.

Figure 8:
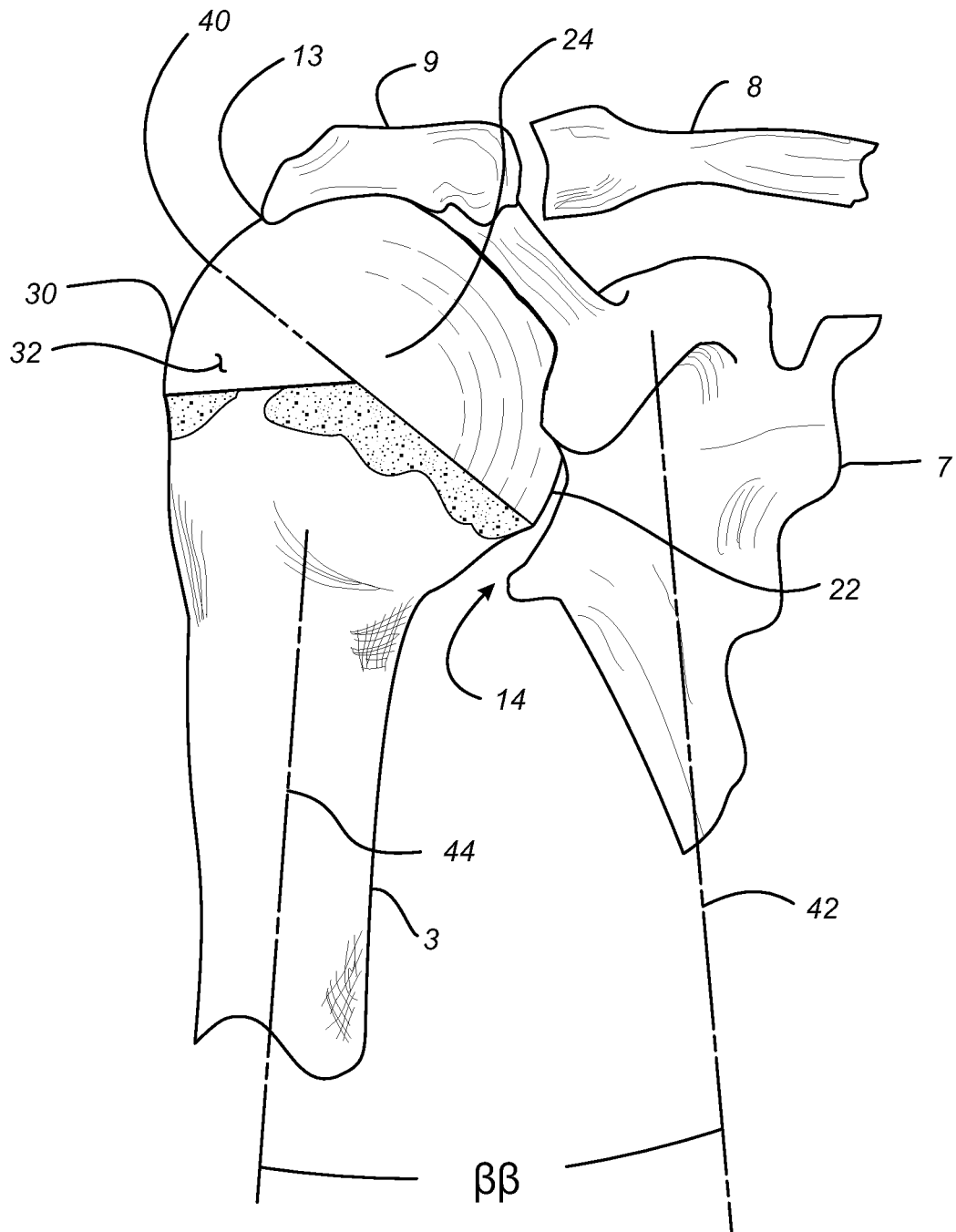
FIG. 8 is a plan view of the extended head humeral prosthesis of FIGS. 1 and 7 shown in position implanted on a diseased humerus and in cooperation with the glenoid cavity shown in the retracted position.
Figure 9:
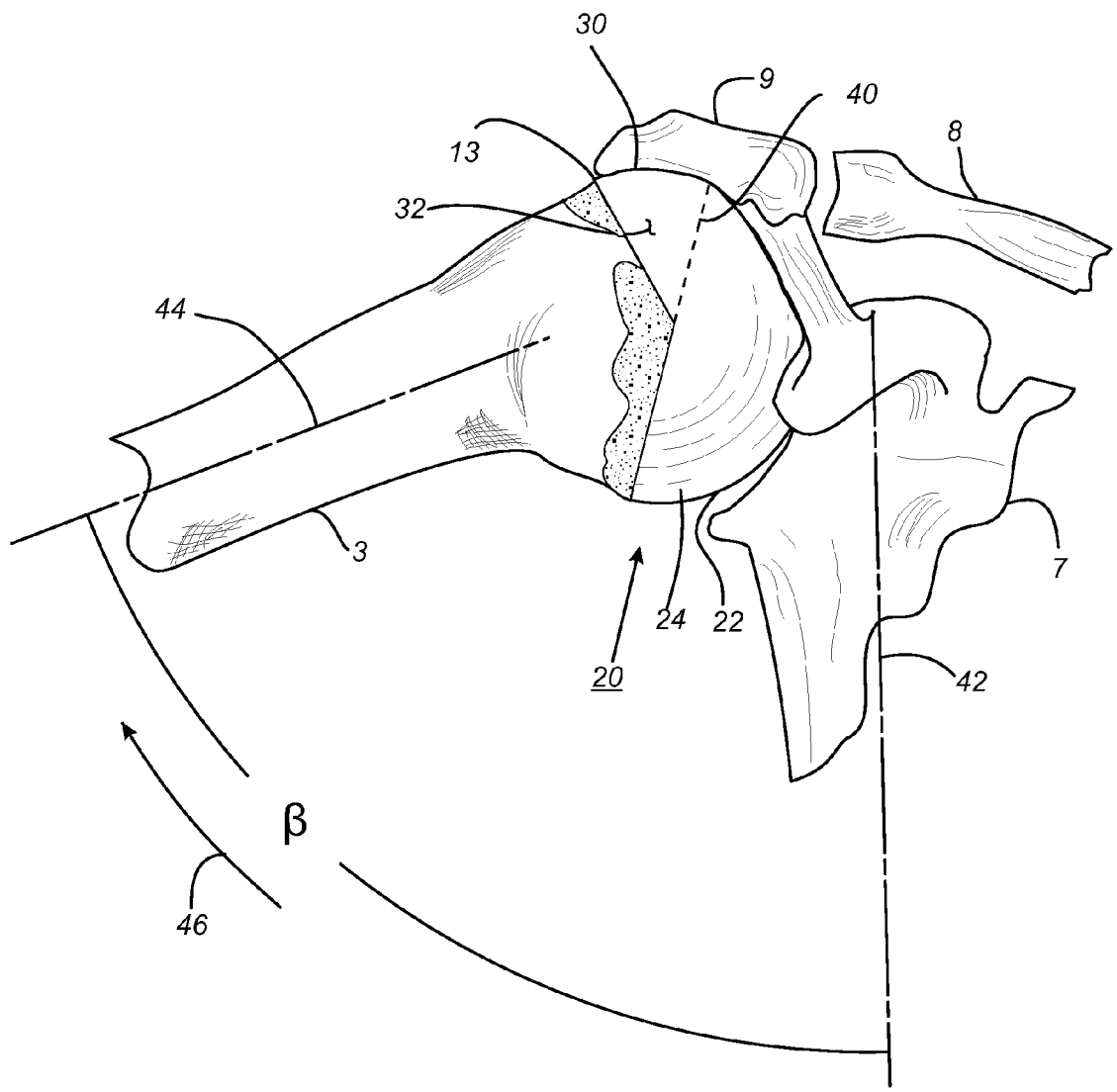
FIG. 9 is a plan view of the extended head humeral prosthesis of FIGS. 1 and 7 shown in position implanted on a diseased humerus and in cooperation with the glenoid cavity shown in the abducted position free from impingement in the glenoid cavity.

Referring now to FIGS. 8 and 9, the humerus 3 is again shown in position with the adjacent skeletal structure. In FIG. 8, the long bone or humerus 3 is shown in position when the upper arm is in position against the torso. At the humeral position as shown in FIG. 8, the angle β between the vertical centerline 42 and humeral centerline 44 is represented by an angle ββ of approximately 15 degrees. In this position of the humerus 3, it can be seen that the acromion 9 is in contact with the first articulating surface 24 at acromion distal edge or outer edge 13.

Referring now to FIG. 9, the humerus 3 is shown being abducted in the direction of arrow 46 with the respective angle β equaling approximately 60 degrees. In this abducted position, the outer edge 13 of the acromion 9 is in a position such that the second articulating surface 32 of the second body 30 is used to provide a smooth articulating surface for the outer edge 13 of the acromion 9.

Figure 10:
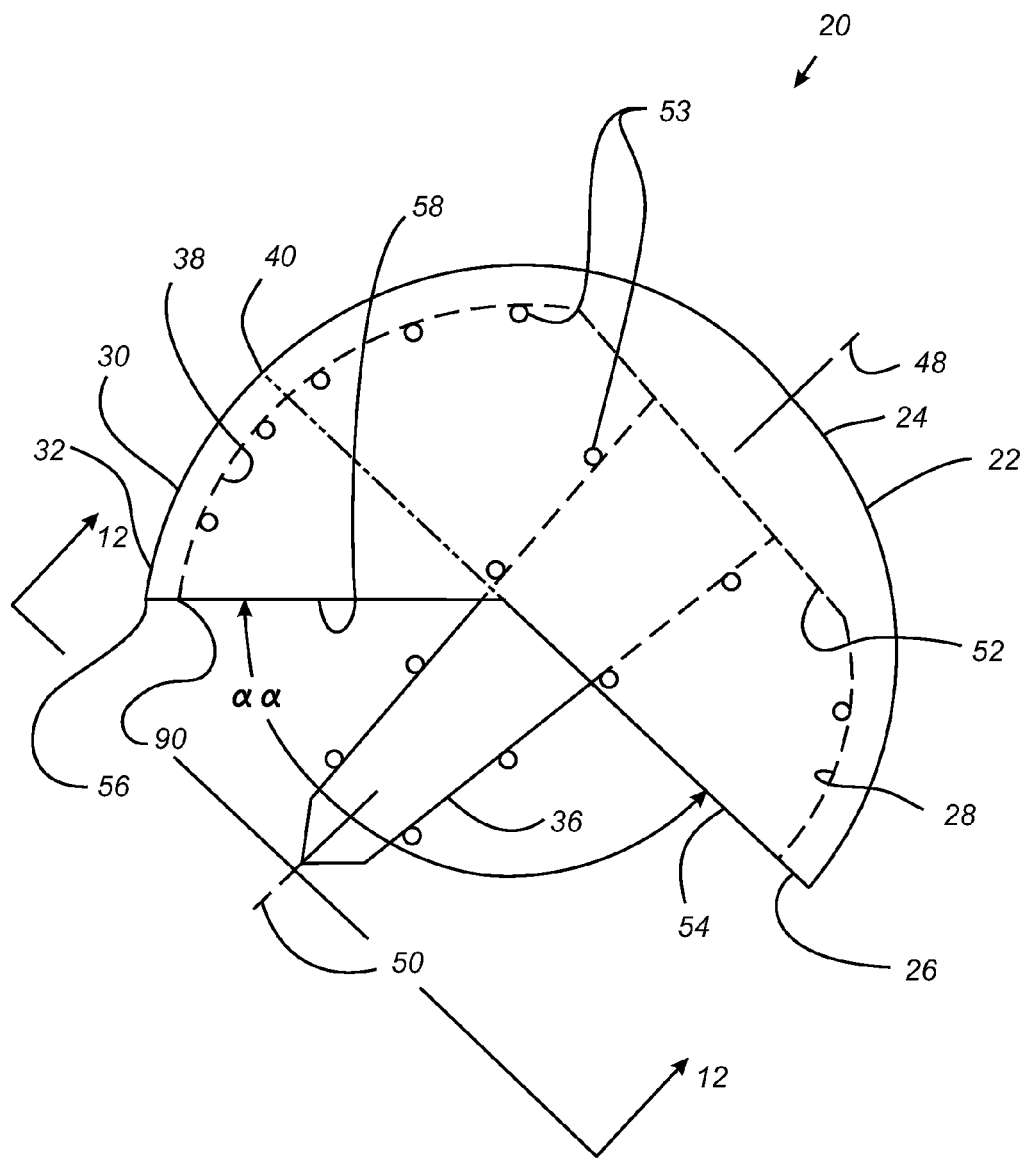
FIG. 10 is an enlarged plan view of the extended head humeral prosthesis of FIGS. 1 and 7.

Referring now to FIG. 10, the prosthesis 20 is shown in greater detail. While the stem 36 of the prosthesis 20 may have any suitable shape capable of providing support for the prosthesis 20 in the humerus 3, preferably, and as shown in FIG. 10, the stem 36 has a general cylindrical shape. The first body 22 as shown in FIG. 10 may be in the form of a hollow hemisphere having a first longitudinal body centerline 48. The stem 36 has a stem longitudinal centerline 50. As shown in FIG. 10, the prosthesis 20 may be such that the first longitudinal body centerline 48 and the stem longitudinal centerline 50 are coincident. Such a configuration provides for a preferred central location of the stem 36.

Applicants have found that since the diseased humerus may become flattened around the humeral head, to provide adequate support to the prosthesis 20 in a diseased humerus, the support surface opposed to the articulating surface 24 of the prosthesis 20 may include at least part of the second surface 28 to include a support surface 52 opposed to the first articulating surface 24. Preferably, for simplicity, the support surface may be generally planar.

To assist the prosthesis 20 in its strength and stability in the humerus 3 and to promote the bony ingrowth around the prosthesis 20, the prosthesis 20 may include a porous coating 53 secured to, for example, the second surface 28 of the first body 22, the second surface 38 of the second body, the planar portion 52 of the second surface 28, as well as on the periphery of the stem 36. Any commercially available porous coating will assist in the bony ingrowth of the prosthesis 20 to the humerus 3. One particular porous coating is provided by the assignee of the instant application under the trade name POROCOAT™. Porous coating may be more fully understood by reference to U.S. Pat. No. 3,855,638 to Pilliar, hereby incorporated in its entireties by reference.

Figure 20:
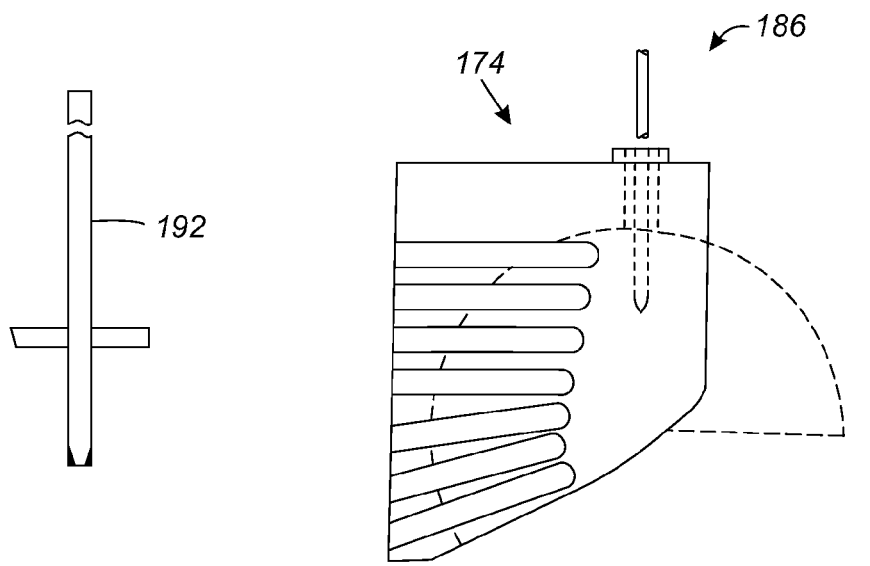
FIG. 20 is plan view of another tool kit for preparing a humeral head for the extended head humeral prosthesis of FIGS. 1 and 7.
Figure 20:
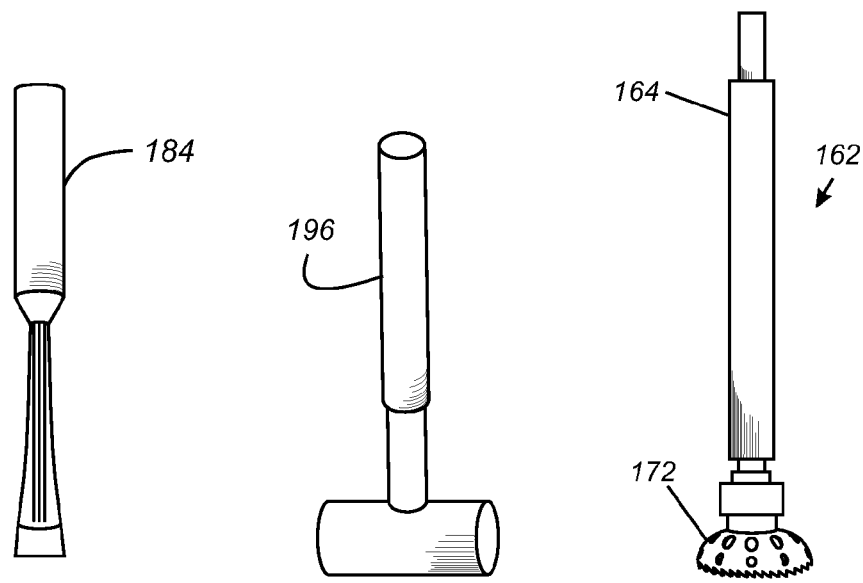

As shown in FIG. 10, the circular outer periphery 26 of the articulating surface 24 of the first body 22 defines a first plane 54. Similarly, the second articulating surface 32 of the second body 30 defines a second surface periphery 56. The second surface periphery 56 defines a second plane 58. The first plane 54 and the second plane 58 are non-coincident. The first plane 54 and the second plane 58, therefore, define an angle αα there between. As shown in FIG. 10, the angle αα is obtuse. While the angle αα may approach 180 degrees, the angle aa may likewise have a range of about 120 to 180 degrees. As shown in FIG. 20, the angle aa may be around 138 degrees.

Figure 11:
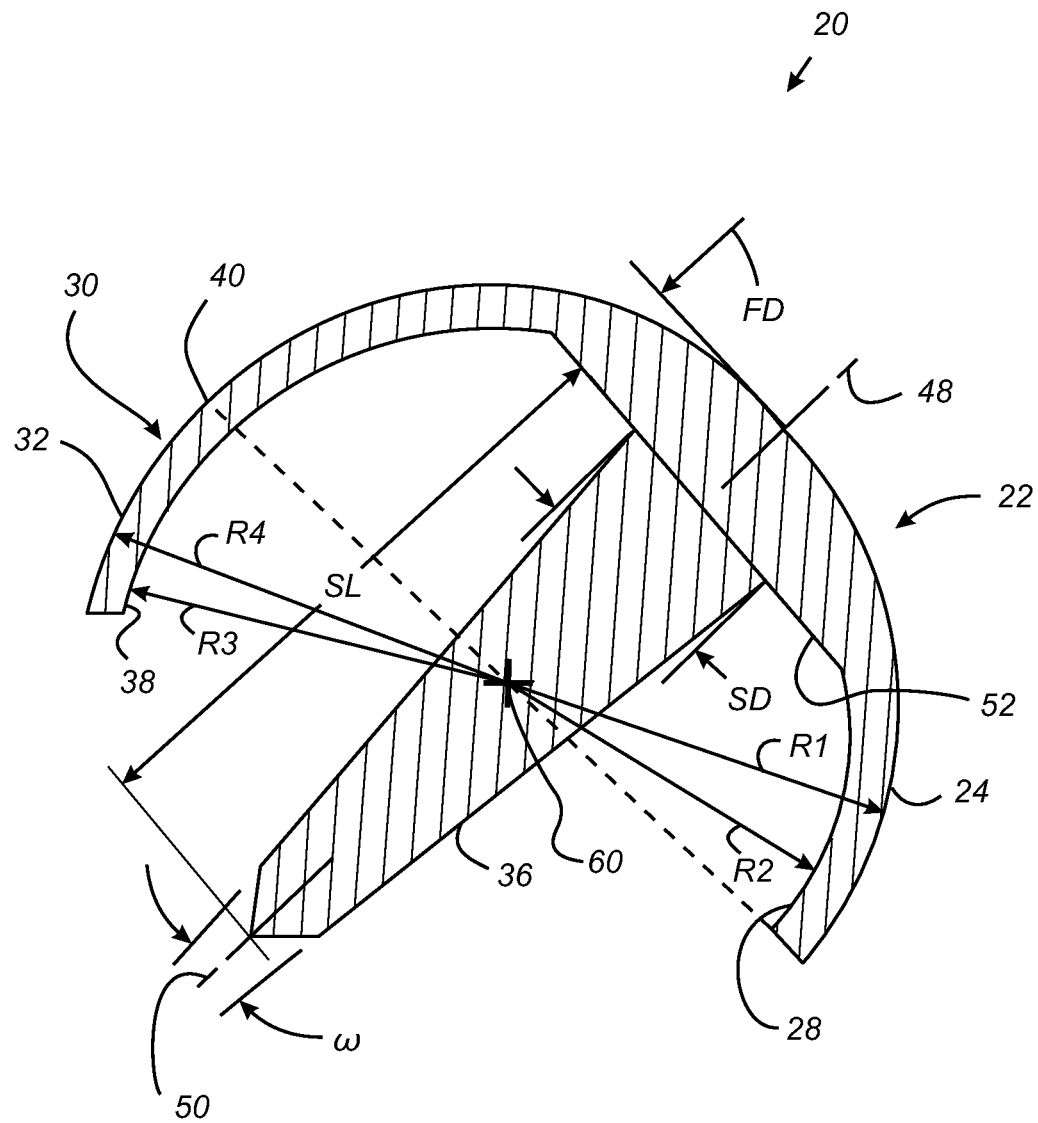
FIG. 11 is a cross sectional view of the extended head humeral prosthesis of FIG. 10.
Figure 12:
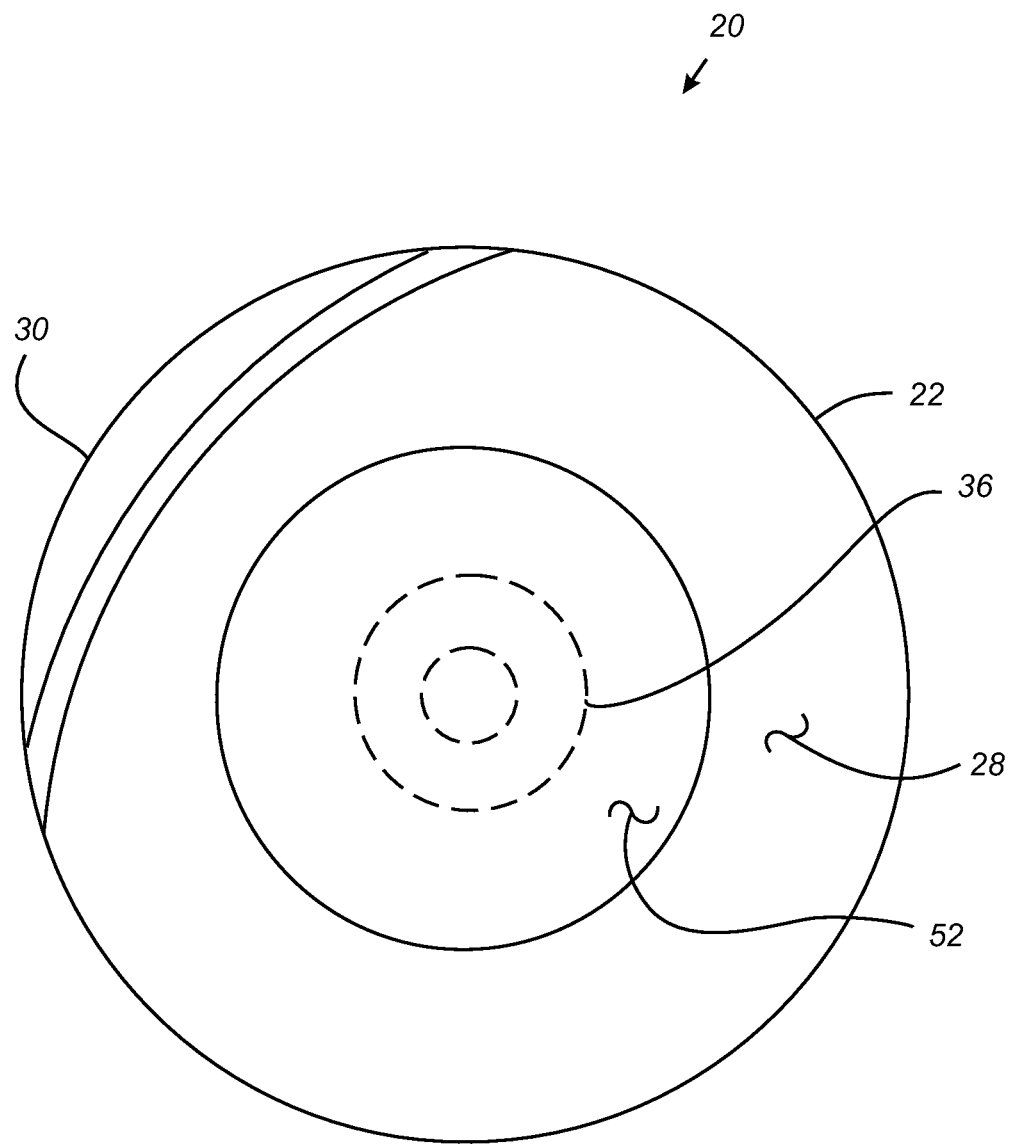
FIG. 12 is an auxiliary view of the extended head humeral prosthesis of FIG. 10 along the lines 12-12 in the direction of the arrows.

Referring now to FIGS. 11 and 12, the prosthesis 20 is shown in greater detail. As shown in FIG. 11, the stem 36 may be generally cylindrical having stem diameter SD and a length SL. The stem 36 may be tapered and defined by an angle ω. The angle ω may be around 5 to 30 degrees.

The planar portion 52 of the prosthesis 20 may have any reasonable location with respect to the articulating surface 24 of the prosthesis 20. The proper position of the planar portion 52 will depend on the flattening of the humeral head and how much corresponding amount of resection may be required to the humeral head. The position of the planar portion 52 with respect to the articulating surface 24 may be defined by a flat dimension FD.

The hemispherical body 22 and second body 30 of the prosthesis 20 may be defined with respect to a prosthetic center point 60. The articulating surface 24 may be defined by a radius R1 extending from center point 60 the articulating surface 24. The second surface 28 may be defined by a radius R2 extending from the prosthetic center point 60 to the second surface 28. Similarly, the second articulating surface 32 may be defined by radius R4 from the prosthetic center point 60 to the second articulating surface 32. Similarly, the second surface of the second body 38 may be defined by radius R3 from the prosthetic center point 60 to the second surface 28. For simplicity, the radii R1 and R4 may be identical and for simplicity the radii R2 and R3 may be identical.

Referring now to FIG. 12, the underside of the prosthesis 20 is shown.

The prosthesis 20 may have any size compatible with the humerus. Preferably, and as shown in FIGS. 7 through 12, the prosthesis 20 preferably blends with the periphery of the humerus. Thus, the size of the prosthesis 20 is governed generally by the size of the anatomical humerus.

The prosthesis 20 may be made of any suitable durable material that is compatible with the human anatomy. For example, the prosthesis 20 may be made of a ceramic, a plastic or a metal. If made of a metal, the prosthesis 20 may be made, for example, of a cobalt chromium alloy, a titanium alloy, or a stainless steel alloy.

Figure 16:
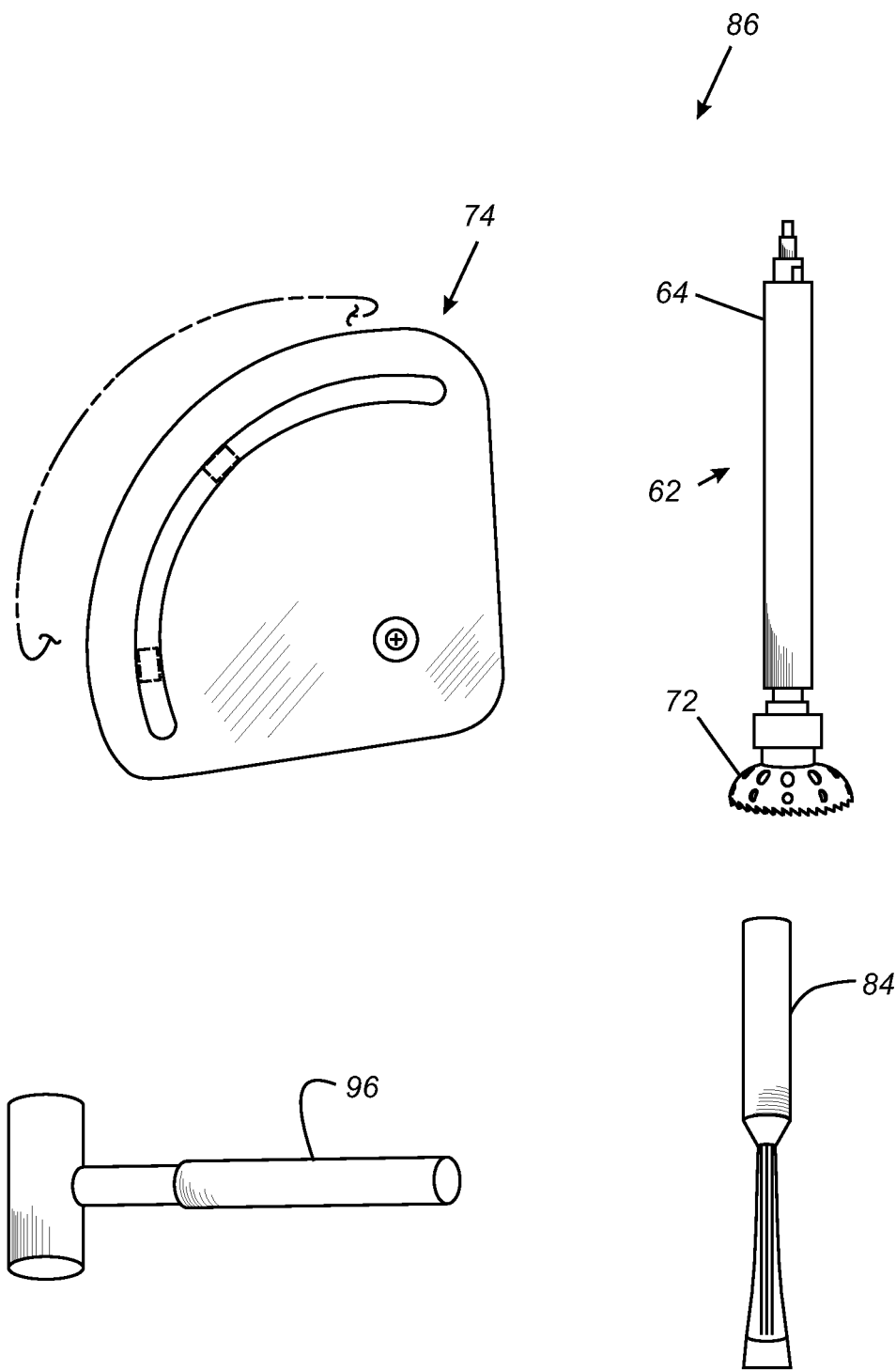
FIG. 16 is plan view of a tool kit for preparing a humeral head for the extended head humeral prosthesis of FIGS. 1 and 7.

Referring now to FIG. 16, an instrument in the form of, for example, a reamer assembly 62 is shown for use in reaming, for example, the articulating surface 24 of the prosthesis 20 of FIG. 7.

Figure 13:
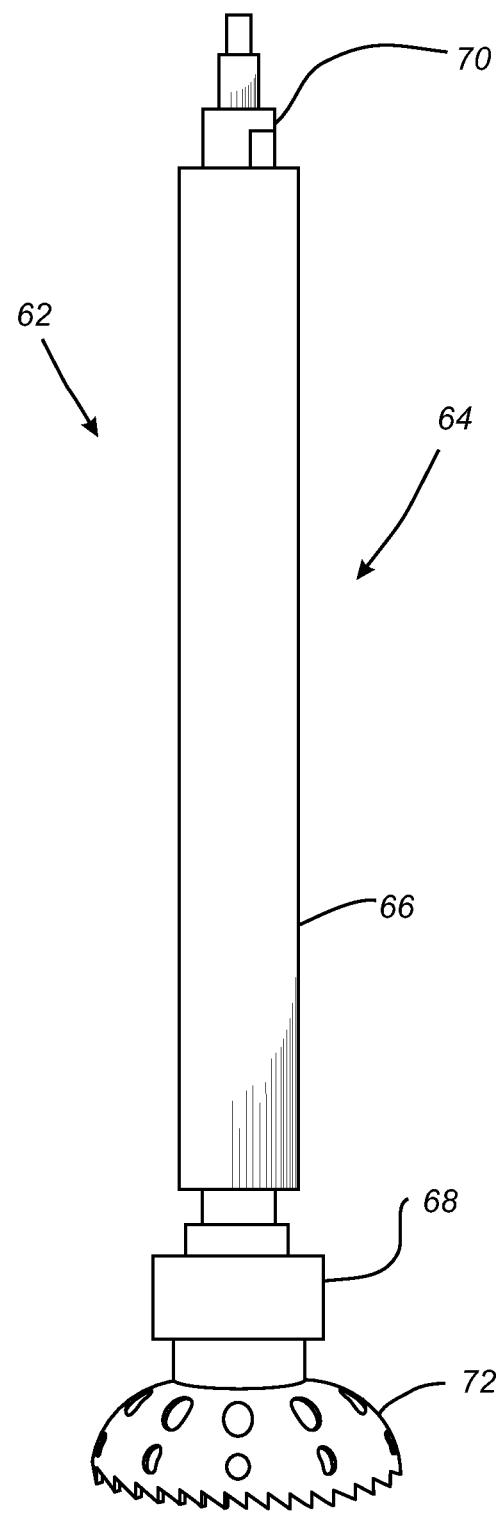
FIG. 13 is a plan view of a reamer assembly to prepare a humeral head for the extended head humeral prosthesis of FIGS. 1 and 7.

As shown in FIG. 13, the reamer assembly 62 includes a tool driver 64. The tool driver 64 includes a body 66 having a cutting tool adaptor 68 and a drive adapter 70. The reamer assembly 62 also includes a reamer 72. The reamer 72 is connected to the tool driver 64 by the cutting tool adapter 68. The reamer 72 may be a hemispherical grater type reamer.

Figure 14:
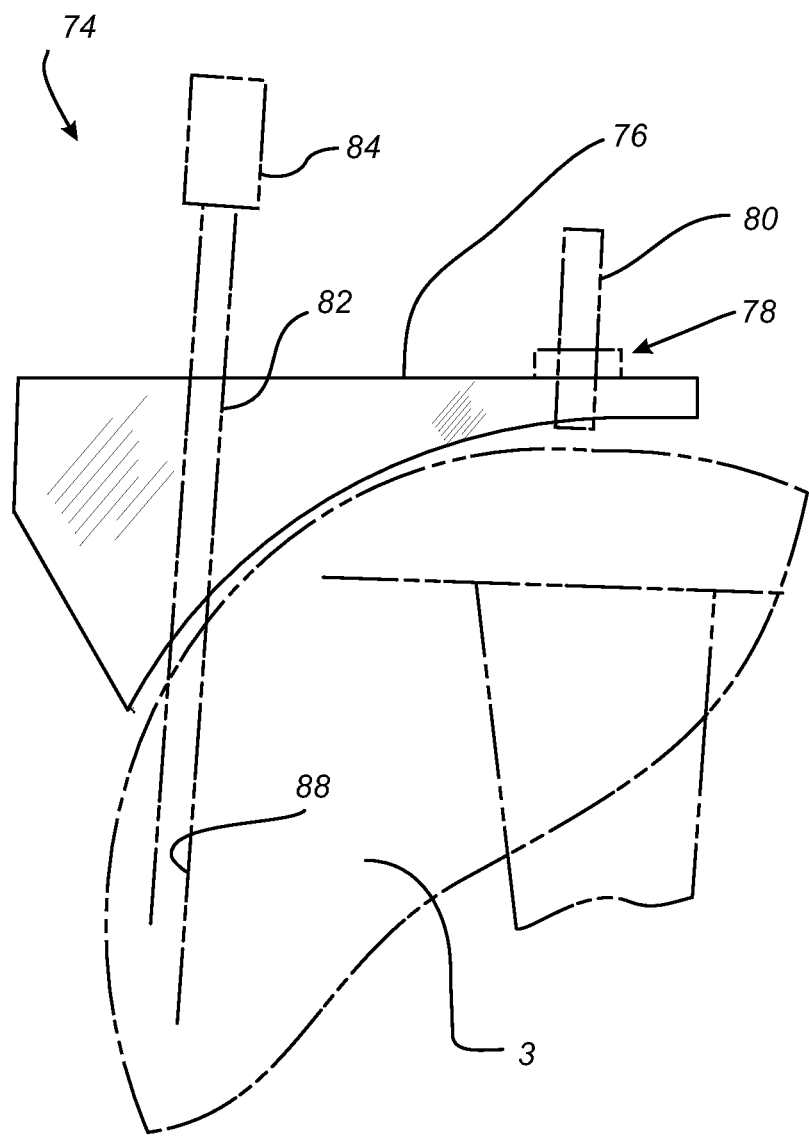
FIG. 14 is a plan view, partially in cross section of a cutting guide for use with a cutter to prepare a humeral head for the extended head humeral prosthesis of FIGS. 1 and 7.
Figure 15:
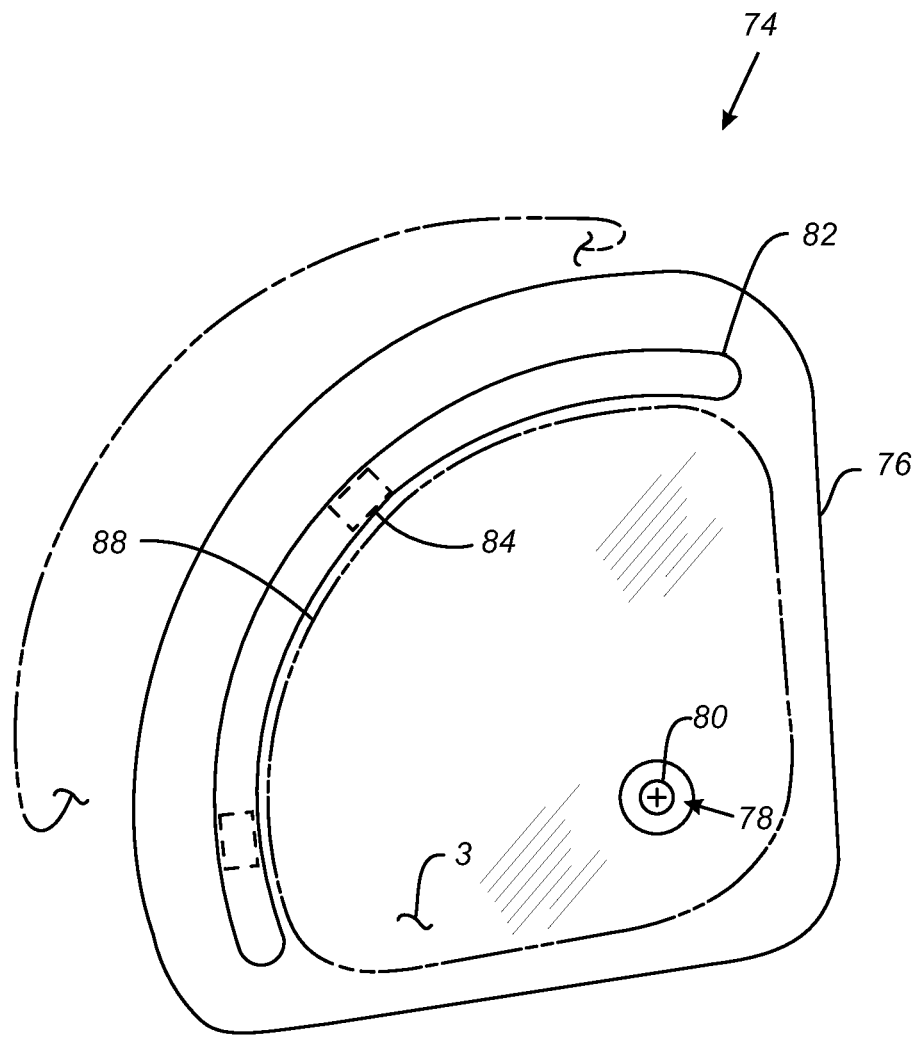
FIG. 15 is a top view of the cutting guide of FIG. 14.

Referring now to FIGS. 14 and 15, a bone cutting tool guide 74 is shown. The tool guide 74 may include a body 76 having a cylindrical bore 78 for receiving a guide pin 80 and a elongated slot 82 for receiving a cutting tool in the form of osteotome 84. The tool guide 74 is used to prepare surface 88 of humerus 3.

Referring now to FIG. 16, a tool kit 86 is shown for preparing a humerus to receive a prosthesis, for example, prosthesis 20 of FIGS. 7 through 12.

As shown in FIGS. 7 through 12, the prosthesis 20 includes the first body 22 having the first articulating surface 24 and an opposed first surface support surface 28. The prosthesis 20 also includes the second body 30 that has the second articulating surface 32 and an opposed second support surface 38.

Referring again to FIG. 16, the kit 86 is used for preparing the first support surface 28 and the second support surface 38. The tool kit 86 of FIG. 16 includes the reamer 72 and may include the tool driver 64 to form the reamer assembly 62. The tool kit 86 further includes a bone cutting tool 84 for preparing a second prepared surface on the humerus 3 for receiving the second support surface 38 of, for example, the prosthesis 20.

As shown in FIG. 15, the bone cutting tool 84 is used to prepare second prepared surface 88 on the humerus 3. As shown in FIG. 15, the second prepared surface 88 represents the inside surface of a cylinder. Such a shape on the humerus is necessary to accommodate the inner edge 90 of the second body 30 of the prosthesis 20. (See FIG. 11).

Preferably and as shown in FIG. 16, the kit 86 further includes the bone cutting tool guide 74 for guiding the osteotome 84 through the elongated slot 82 of the bone cutting tool guide 74. The osteotome 84 may be struck with mallet 96.

Referring now to FIG. 10, it should be appreciated that if the angle αα approaches 180 degrees, it may be possible to provide for the reaming of the humerus with a reamer assembly 62 (see FIG. 13) and merely pivot the reamer assembly 62 to form a contour for both the second surfaces 28 and 38.

It should be appreciated, however, as the angle αα moves from 180 degrees to something less, for example, 140 degrees the inner edge 90 of second body 30 of prosthesis 20 (see FIG. 11) moves closer to the stem centerline 50 such that a generally hemispherical grater-type reamer such as that of FIG. 13 may not be appropriate to prepare the hemispherical head of the humerus. Therefore, the guide 74 of the kit 86 provides for a surface 88 that is generally cylindrical to permit the corner 90 of the prosthesis 20 to be fully seated into the humerus.

It should be appreciated that the bone cutting tool necessary to prepare the humerus may include a drill, a reamer, a broach, a saw or an osteotome.

Figure 17:
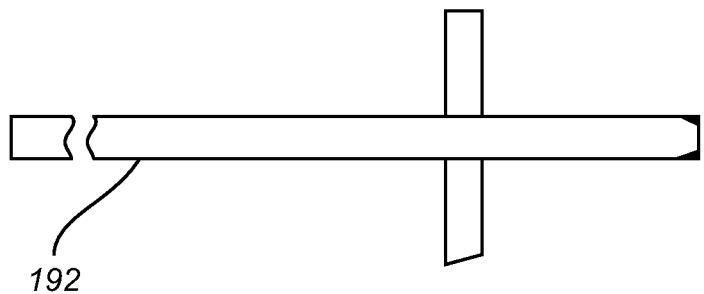
FIG. 17 is plan view of an end mill for preparing a humeral head for the extended head humeral prosthesis of FIGS. 1 and 7.

Referring now to FIGS. 17 through 20, an alternate tool kit 186 for preparing a humerus is shown. Referring first to FIG. 17, end mill 192 is shown. End mill 192 may be any commercially available milling cutter capable of end cutting.

Figure 18:
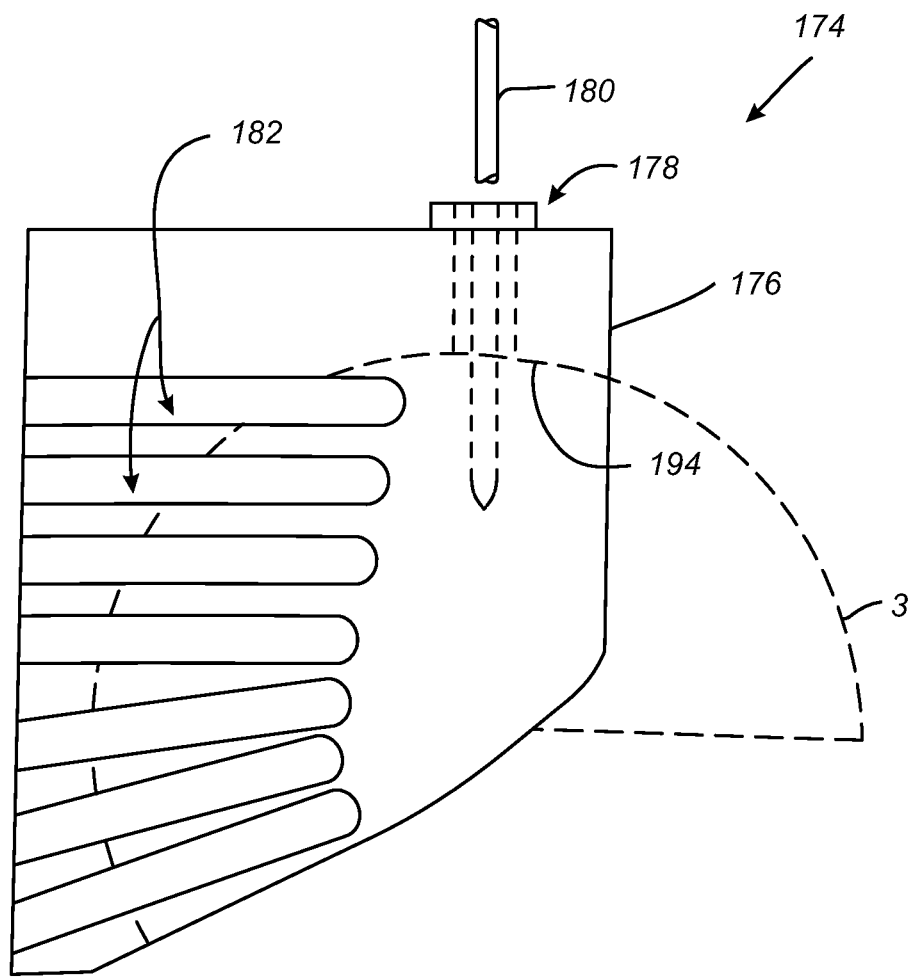
FIG. 18 is a plan view of another cutting guide for use with a cutter to prepare a humeral head for the extended head humeral prosthesis of FIGS. 1 and 7.
Figure 19:
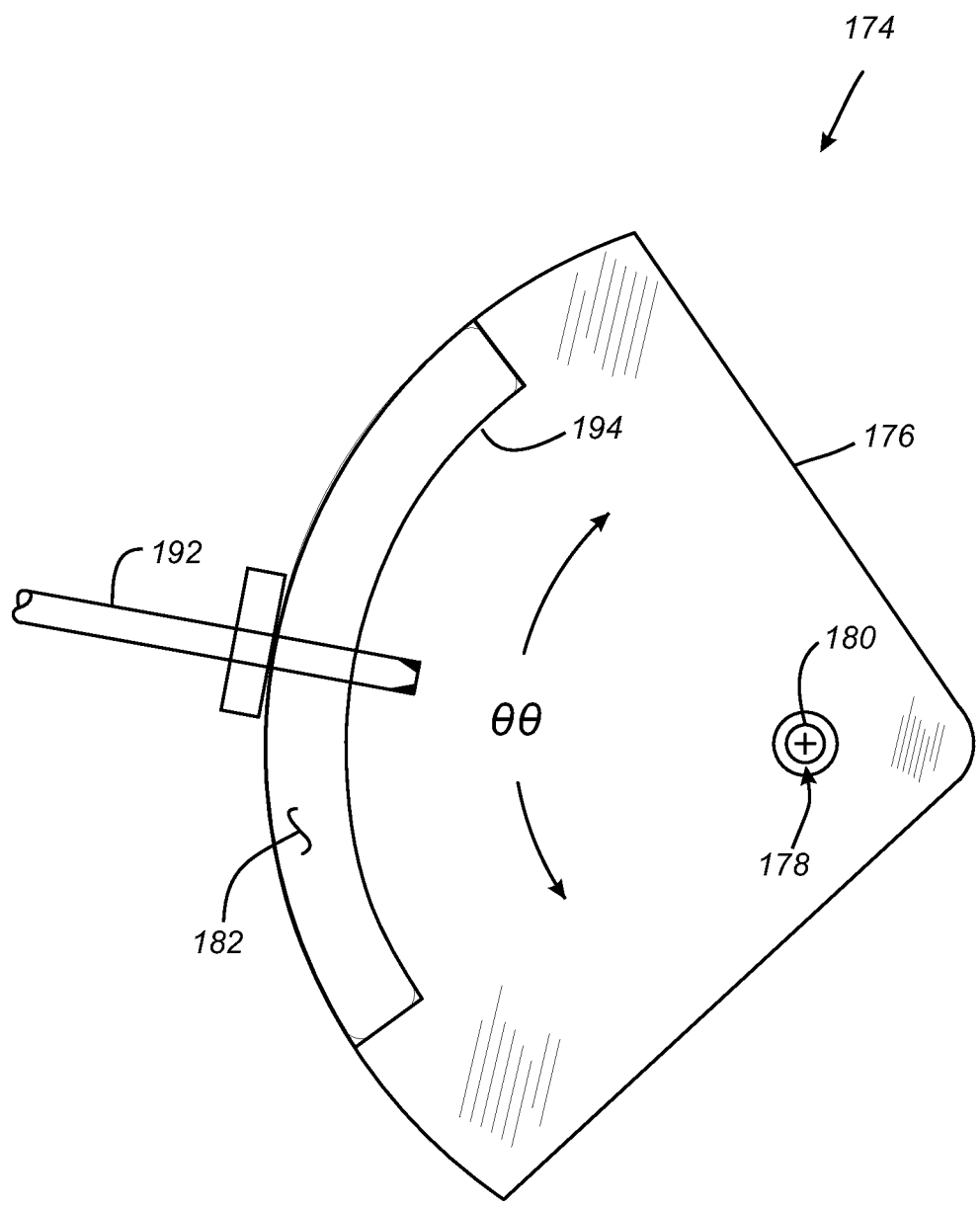
FIG. 19 is a top view of the cutting guide of FIG. 18.

Referring now to FIGS. 18 and 19, a bone cutting tool guide 174 is shown for use with the end mill 192 of FIG. 17. The guide 174 includes a body 176. The body 176 includes an opening 178 for cooperation with location pin 180. The location pin 180 is used to orient the guide 174 with respect to the humerus 3. The guide 174 further defines a plurality of slots 182 formed in the body 176.

Referring to FIG. 19, the slots 182 extend an angle θθ about the periphery of concave inner surface 194 of the guide 174. The slots 182 are aligned somewhat parallel to each other and slightly spaced apart. The slots 182 are close enough to minimize the amount of material not covered by the slots but far enough apart to provide enough strength to the guide 174, particularly around the slots 182.

Referring now to FIG. 20, the kit 186 is shown. The kit 186 includes reamer assembly 162 for preparing the first prepared surface on the humerus. The reamer assembly 162 is similar to reamer assembly 62 of FIG. 13 and includes a tool driver 164 similar to the tool driver 64 of FIG. 13 as well as a grater type hemispherical reamer 172 similar to the reamer 72 of the reamer assembly 62 of FIG. 13. The kit 20 further includes end mill 192 as well as an osteotome 184 similar to osteotome 84 of the kit 86 of FIG. 16. The osteotome 184 serves to remove the material remaining after the end mill 192 removes materials in alignment with the slots 182 of the guide 174. Preferably and as shown in FIG. 20, the kit 186 may further include the guide 174. Further, the kit 20 may include a surgical mallet 196. The surgical mallet 196 is used to strike the osteotome 184.

Figure 21:
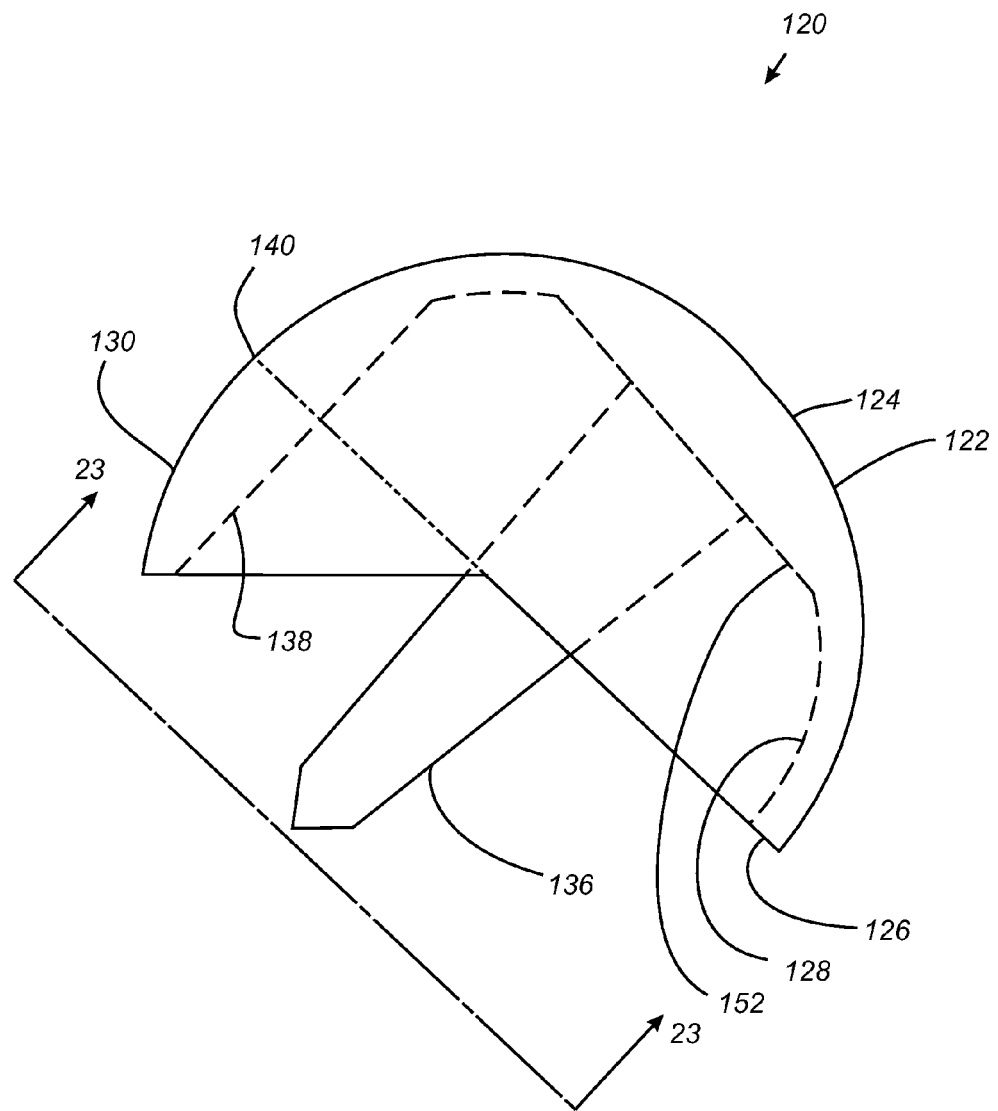
FIG. 21 is a plan view of another embodiment of a extended head humeral prosthesis according to the present invention.
Figure 22:
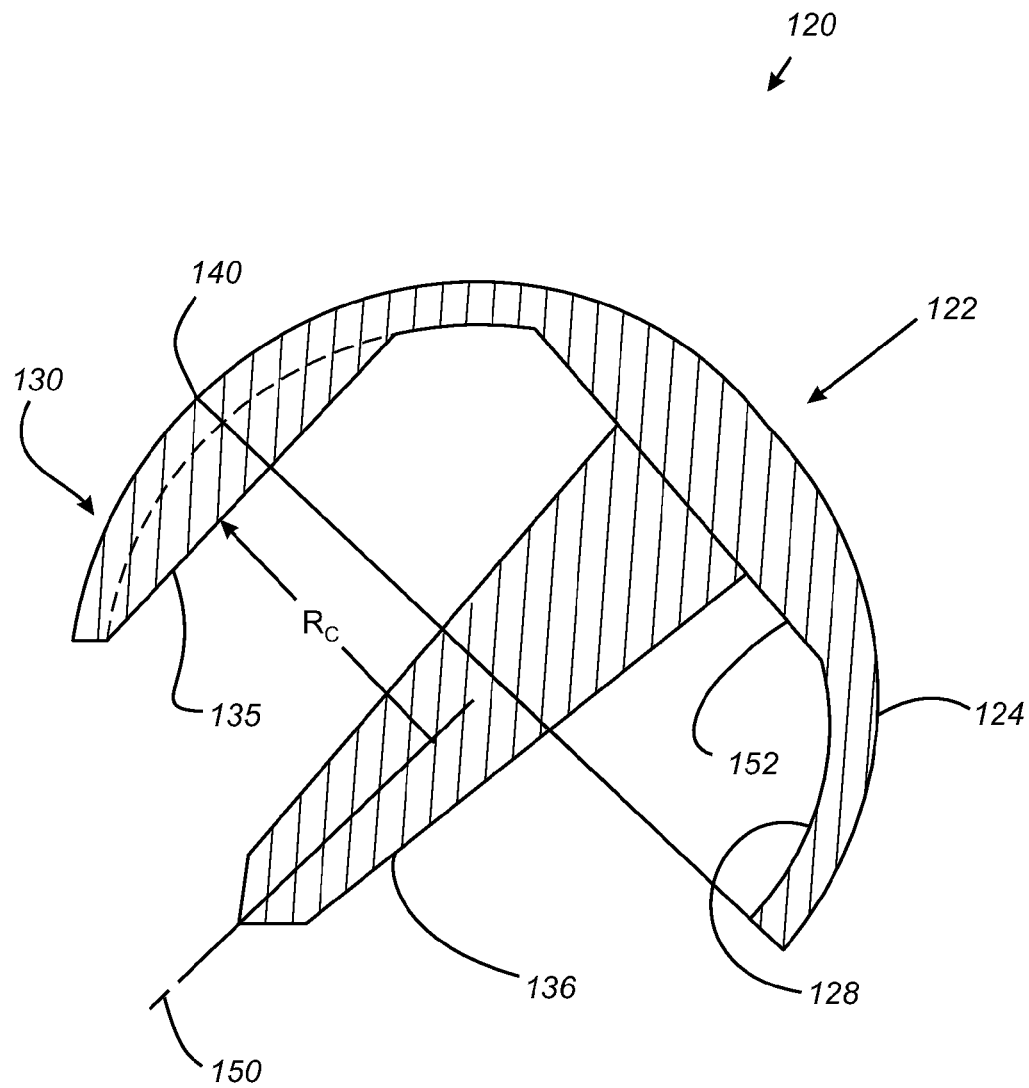
FIG. 22 is a cross sectional view of the extended head humeral prosthesis of FIG. 21.
Figure 23:
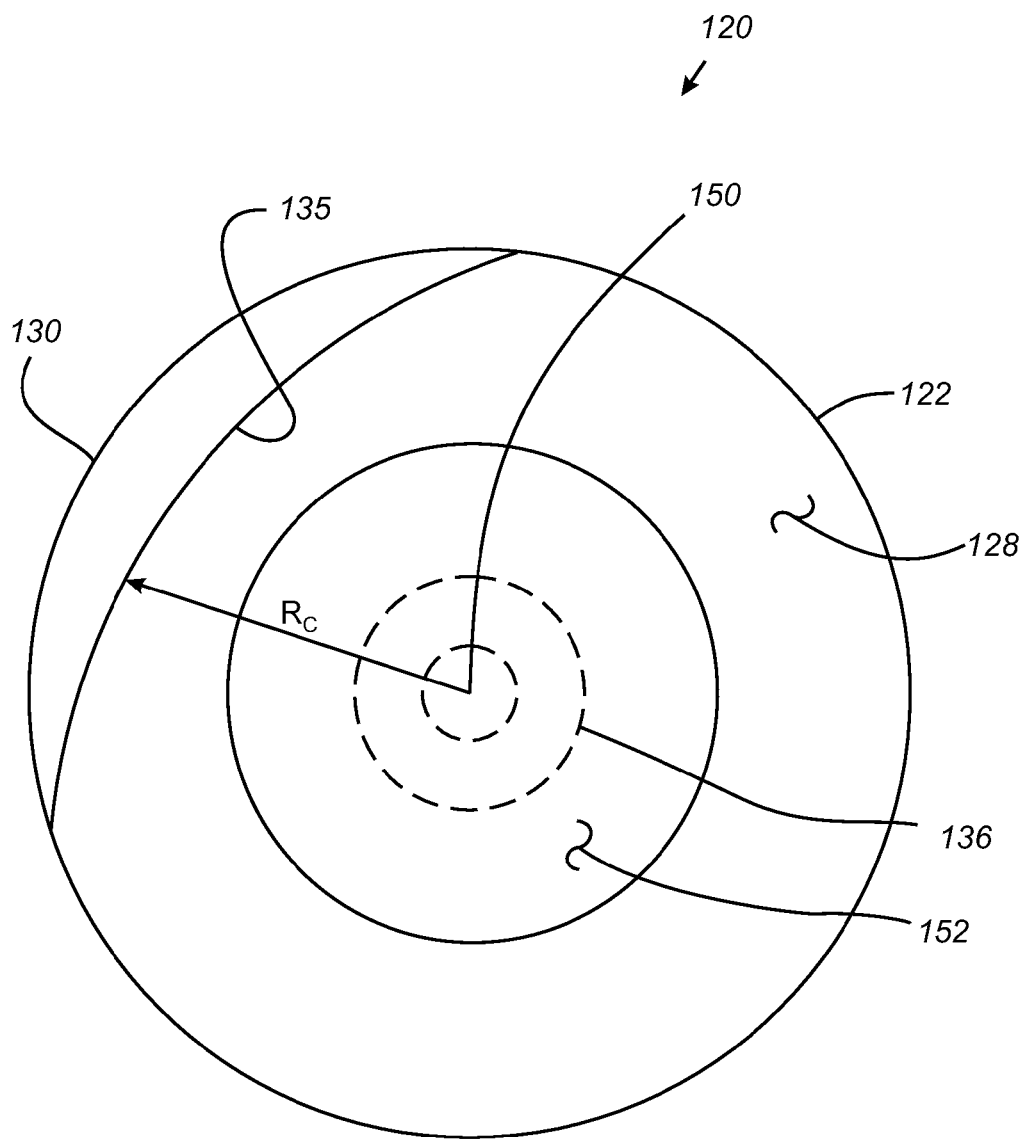
FIG. 23 is an auxiliary view of the extended head humeral prosthesis of FIG. 21 along the lines 23-23 in the direction of the arrows.

Referring now to FIGS. 21, 22 and 23, an alternate embodiment of the present invention is shown as prosthesis 120. Prosthesis 120 is similar to prosthesis 20 of FIGS. 7 through 12 except that prosthesis 120 is designed to take into consideration the limit in installing the prosthesis onto the prepared humeral head. Mainly, the prosthesis 120 takes into consideration the inability to clear the edge 90 of the prosthesis 20 when utilizing a spherically shaped humeral head.

Referring now to FIG. 21, the prosthesis 120 includes a first body 122 having a hemispherical articulating surface 124 and an opposed concave arcuate surface 128. The first body 122 also has a planar portion 152 opposing the articulating surface 124. The prosthesis 120 further includes a tapered cylindrical stem 136 extending inwardly from the planar portion 152 of the first body 122. The prosthesis 120 further includes a second body 130 extending from circular outer periphery 126 of the first body 122. A boundary portion 140 is located between the first body 122 and the second body 130 and is preferably smooth and continuous. Unlike the prosthesis 20, the second body 130 of the prosthesis 120 has an opposed surface in the form of a cylindrical inner periphery 138. The cylindrical periphery 138 is designed to matingly fit with the cylindrical surface prepared on the humeral head.

Referring now to FIG. 22, the cylindrical periphery 138 is shown in greater detail. The cylindrical periphery 138 is defined by a radius $R_c$ extending from stem centerline 150.

Referring now to FIG. 23, another view of the cylindrical periphery 135 of the prosthesis 120 is shown. The cylindrical periphery 135 is again defined by a radius $R_c$ from stem centerline 150.

Figure 24:
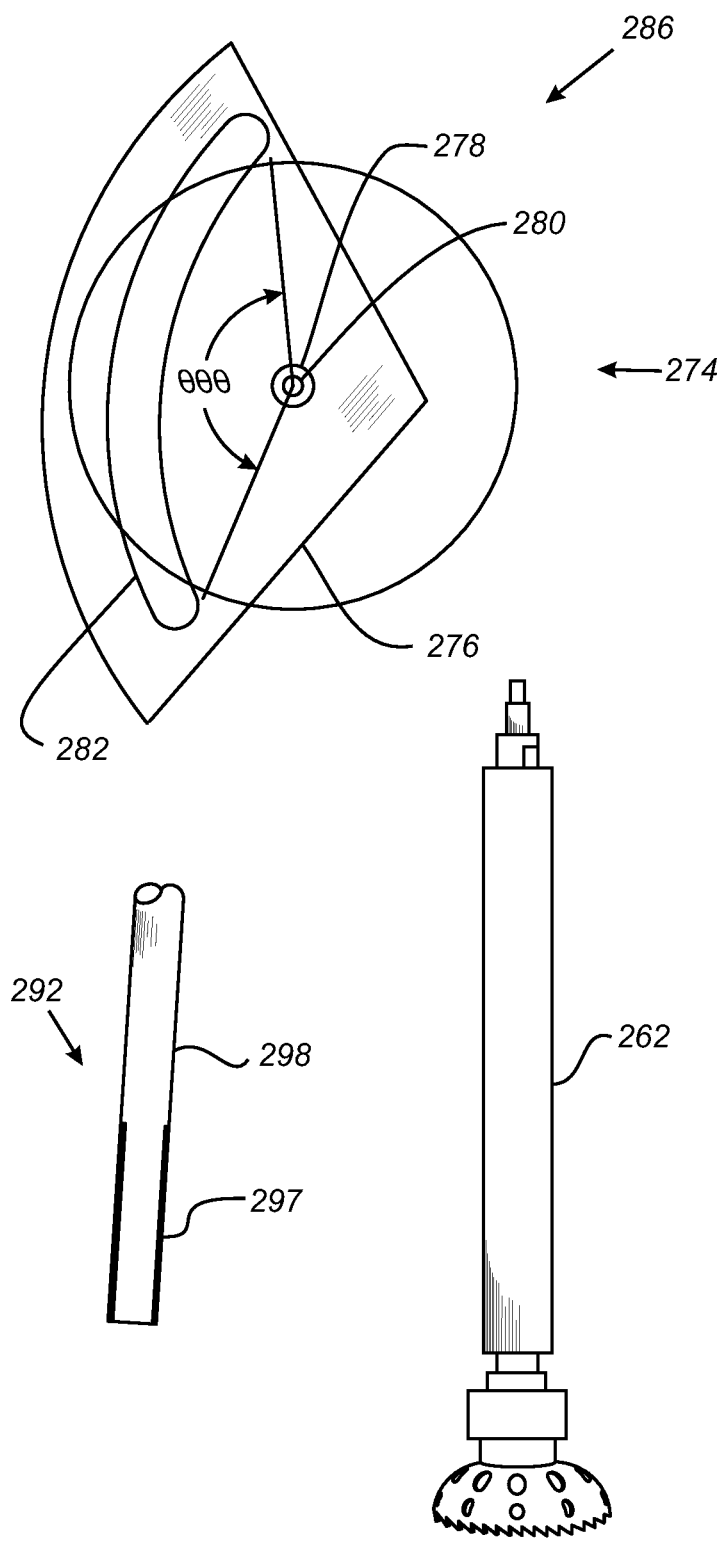
FIG. 24 is a plan view of a tool kit for preparing a humeral head for the extended head humeral prosthesis of FIGS. 21-23.

Referring now to FIG. 24, an alternate tool kit is shown as tool kit 286. The tool kit 286 is used to prepare a humerus for the prosthesis of the present invention. The tool kit 286 includes a reamer assembly 262 similar to the reamer assembly 162 of the kit 186 of FIG. 20. The tool kit 286 further includes a cylindrical end cutting reamer 292 having a cylindrical cutting surface 297 and a guiding surface 298. The kit 286 further includes a guide 274 for guiding the cylindrical reamer 292 in a proper path to properly prepare the humerus. The guide 274 includes a body 276 defining an opening 278 for cooperation with location pin 280, which is utilized to properly position the guide 274 on the humerus. The body 276 of the guide 274 further includes an arcuate elongated slot 282 that cooperates with the guiding surface 298 of the reamer 292 to guide the reamer along a proper path. The arcuate slot 282 is defined by an included angle θθ.

Figure 25:
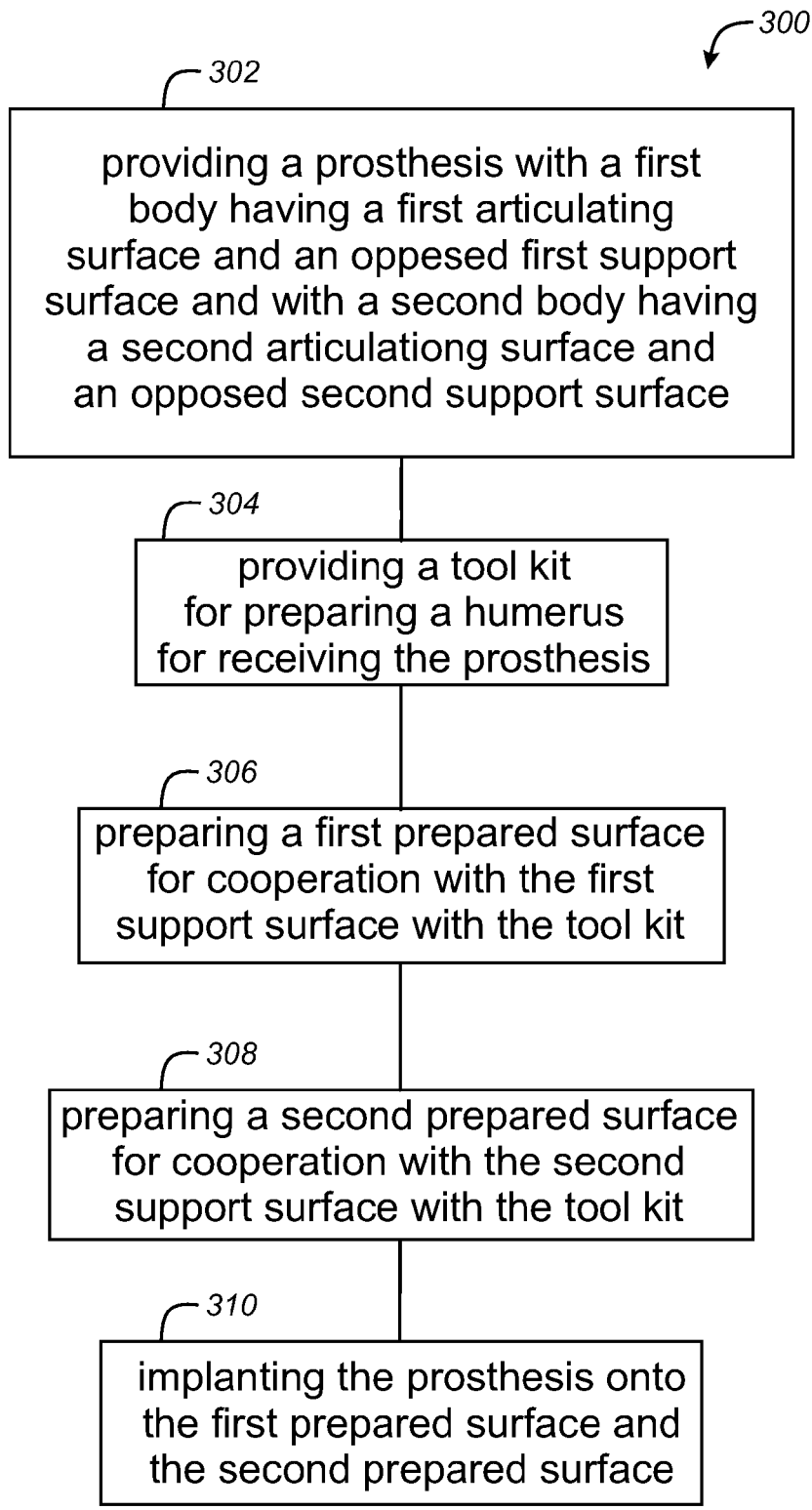
FIG. 25 is a process flow chart for a method of performing shoulder arthroplasty surgery according to another embodiment of the present invention.

Referring now FIG. 25, an alternate embodiment of the present invention is shown as surgical method 300. The method 300 includes the first step 302 of providing a prosthesis with a first body having a first articulating surface and an opposed first support surface and with a second body having a second articulating surface and an opposed second support surface. The method 300 further includes a second step 304 providing a tool kit for preparing a humerus for receiving the prosthesis. The method 300 further includes a third step 306 of preparing a first prepared surface for cooperation with the first support surface with the tool kit. The method 300 also includes a fourth step 308 of preparing a second prepared surface for cooperation with the second support surface with the tool kit. The method 300 further includes a fifth step 310 of implanting the prosthesis onto the first prepared surface and the second prepared surface.

Although the present invention and its advantages have been described in detail, it should be understood that various changes, substitutions, and alterations can be made therein without departing from the spirit and scope of the present invention as defined by the appended claims.

What is claimed is:

1. A tool kit for preparing a humerus to receive a prosthesis with a first body having a first articulating surface and an opposed first support surface and with a second body having a second articulating surface and an opposed second support surface, said tool kit comprising:
   a reamer for preparing a first prepared outer surface portion on the humerus for receiving the first support surface;
   a bone cutting tool for preparing a second prepared outer surface portion on the humerus for receiving the second support surface;
   a mallet, wherein the bone cutting tool is configured to be struck by the mallet; and
   a guide configured to guide the position of said bone cutting tool.

2. The tool kit of claim 1, wherein the bone cutting tool is configured to prepare a generally cylindrical second prepared outer surface.

3. The tool kit of claim 2, wherein the reamer is configured to prepare a generally hemispherical first prepared outer surface.

4. A tool kit for preparing a humerus to receive a prosthesis with a first body having a first articulating surface and an opposed first support surface and with a second body having a second articulating surface and an opposed second support surface, said tool kit comprising:
   a reamer for preparing a first prepared outer surface portion on the humerus for receiving the first support surface; and
   a bone cutting tool for preparing a second prepared outer surface portion on the humerus for receiving the second support surface, wherein the bone cutting tool is configured to prepare a generally cylindrical second prepared outer surface.

5. The tool kit of claim 4, wherein said bone cutting tool comprises one of a drill, a reamer, a broach, a saw and an osteotome.

6. The tool kit of claim 5,
   wherein said bone cutting tool comprises an end cutting reamer for preparing a plurality of channels in the humerus; and
   further comprising a guide for controlling the position and depth of said reamer.

7. The tool kit of claim 4, further comprising a guide for controlling the position of said bone cutting tool.

8. The tool kit of claim 7, wherein the guide comprises:
   an elongated slot configured to receive a portion of the bone cutting tool.

9. The tool kit of claim 8, wherein the reamer is configured to prepare a generally hemispherical first prepared outer surface.

10. The tool kit of claim 8, wherein the elongated slot is a generally arcuate elongated slot.

11. The tool kit of claim 10, further comprising:
    a mallet, wherein the bone cutting tool is configured to be struck by the mallet.

12. The tool kit of claim 11, further comprising a tool driver portion configured to rotationally drive the reamer.

13. The tool kit of claim 12, wherein the reamer is a hemispherical grater type reamer.

14. The tool kit of claim 4, wherein the reamer is configured to prepare a generally hemispherical first prepared outer surface.

15. A tool kit for preparing a humerus to receive a prosthesis with a first body having a first articulating surface and an opposed first support surface and with a second body having a second articulating surface and an opposed second support surface, said tool kit comprising:
    a reamer for preparing a first prepared outer surface portion on the humerus for receiving the first support surface; and
    a bone cutting tool for preparing a second prepared outer surface portion on the humerus for receiving the second support surface; and
    a guide for controlling the position of said bone cutting tool, wherein the guide comprises a generally arcuate elongated slot configured to receive a portion of the bone cutting tool.

16. The tool kit of claim 15, wherein the bone cutting tool is configured to prepare a generally cylindrical second prepared outer surface.

17. The tool kit of claim 16, wherein the reamer is configured to prepare a generally hemispherical first prepared outer surface.

18. The tool kit of claim 15, further comprising:
    a mallet, wherein the bone cutting tool is configured to be struck by the mallet.

19. The tool kit of claim 18, further comprising a tool driver portion configured to rotationally drive the reamer.

20. The tool kit of claim 19, wherein the reamer is a hemispherical grater type reamer.

* * * * *